United States Patent [19]
Gould et al.

[11] Patent Number: 5,470,877
[45] Date of Patent: Nov. 28, 1995

[54] USES OF PERILLIC ACID METHYL ESTER

[75] Inventors: Michael N. Gould, Madison, Wis.; Pamela L. Crowell, Indianapolis, Ind.; Charles E. Elson; Zhibin Ren, both of Madison, Wis.

[73] Assignee: Wisconsin Alumni Research Foundation, Madison, Wis.

[21] Appl. No.: 213,408

[22] Filed: Mar. 15, 1994

Related U.S. Application Data

[63] Continuation-in-part of Ser. No. 865,561, Apr. 9, 1992.

[51] Int. Cl.$^6$ .................... A61K 31/215; A61K 31/045
[52] U.S. Cl. .................................... 514/529; 514/729
[58] Field of Search ................................ 514/529

[56] References Cited

U.S. PATENT DOCUMENTS 5,110,832   5/1992   Chastain et al. .
5,244,916   9/1993   Bokoch .................................. 514/460

FOREIGN PATENT DOCUMENTS

WO93/14749   5/1993   WIPO .

OTHER PUBLICATIONS

Crowell et al., J of Biol. Chem., vol. 266, No. 26, Sep. 15, 1991, pp. 17679–17685.
Ren, et al., "Inhibition of Ubiquinone and cholesterol synthesis by the monoterpene perillyl alcohol," *Cancer Letters* 76:185–190, 1994.
Gould, M., "*Proposal*: Phase I Evaluation of Perillyl Alcohol (NSC 641066) in Patients With Cancer," distributed in Aug., 1993.
Gould, M., "Perillyl Alcohol (NSC 641066) Summary of Activities in the Development Therapeutics Program, DCT, NCI," distributed in Feb., 1994.
Gould, et al., "Perillyl Alcohol (NSC641066) and Limonene (NSC 844) Summary for the Decision Network," distributed in Feb., 1994.
Abstract 3264, Gould, et al., "Differentiation of neuro–2a cells induced by the monoterpene, perillyl alcohol (POH)," *Proceedings*, Eighty–Fourth Annual Meeting, American Association for Cancer Research May 19–22, vol. 34, Mar., 1993.
Abstract 3265, Ren, et al., "Inhibition of ubiquinone biosynthesis by the monoterpene perillyl alcohol (POH)," *Proceedings*, Eighty–Fourth Annual Meeting, American Association for Cancer Research May 19–22, vol. 34, Mar. 1993.
Abstract 3266, Jirtle, et al., "Increased levels of TGF–β1 and mannose–6–phosphate/insulin–like growth factor–II (M6P/IGF–II) receptor in limonene–induced mammary tumor regression," *Proceedings*, Eighty–Fourth Annual Meeting, American Association for Cancer Research May 19–22, vol. 34, Mar., 1993.
Plenary Session 4: Mechanisms of action of chemopreventive agents: Basic science and clinical applications, Gould, "Chemoprevention of mammary cancer by monoterpenes," *Proceedings*, Eighty–Fourth Annual Meeting, American Association for Cancer Research May 19–22, vol. 34, Mar., 1993.
Abstract 3134, Crowell, et al., "Human metabolism of orally administered d–limonene," *Proceedings*, Eighty–Third Annual Meeting of the American Association for Cancer Research May 20–23, vol. 33, Mar., 1992.
Abstract 3135, Haag, et al., "Enhanced inhibition of protein isoprenylation and tumor growth by perillyl alcohol, an hydroxylated analog of d–limonene," *Proceedings*, Eighty–Third Annual Meeting of the American Association for Cancer Research May 20–23, vol. 33, Mar., 1992.
Gould, M., "Cellular and molecular aspects of the multistage progression of mammary carcinogenesis in humans and rats," *Cancer Biology* 4:161–169, 1993.
Crowell, et al., "Identification of metabolites of the antitumor agent d–limonene capable of inhibiting protein isoprenylation and cell growth," *Cancer Chemother. Pharmacol.* 31:205–212, 1992.
Crowell, et al., "Chemoprevention of mammary carcinogenesis by hydroxylated derivatives of d–limonene," *Carcinogenesis* 13(7):1261–1264, 1992.
Haag, et al., "Limonene–induced Regression of Mammary Carcinomas," *Cancer Research* 52:4021–4026, 1992.
Crowell, et al., "Structure–Activity Relationships Among Monoterpene Inhibitors of Protein Isoprenylation and Cell Proliferation," *Biochemical Pharmacology*, 47:14–15, 1994.
Elegbede, et al., "Inhibition of DMBA–induced Mammary Cnacer By The Monoterpene D–Limonene," *Carcinogenesis*, 5[5]:661–664, (1984).
Elegbede, et al., "Regression Of Rat Primary Mammary Tumors Following Dietary D–Limonene," *JNCI*, 76[2]:323–325 (1986).
Haag, et al., "Limonene–induced Complete Regression Of Rat Mammary Carcinomas," *Proc. Of The Amer. Assoc. For Cancer Research*, 32:402 (Apr. 11, 1991).
Elson, et al., "Anti–carcinogenic Activity Of D–Limonene During The Initiation And Promotion/Progression Stages of DMBA–Induced Rat Mammary Carcinogenesis," *Carcinogenesis*, 9[2]331:332, (1988).
Maltzman, et al., "Ther Prevention Of Nitrosomethylurea–Induced Mammary Tumors D–Limonene And Orange Oil," *Carcinogenesis*, 10[4]:781–783 (1.
Wattenberg, et al., "Inhibition Of 4–(Methylnitrosamino)–1–(3–Pyridyl)–1–Butanone Carcinogenesis In Mice By D–Limonene And Citrus Fruit Oils," *Carcinogenesis*, 12[1]:115–117 (1991).
Van Duuren, et al., "Cocarcinogenic And Tumor–Promoting Agents In Tobacco Carcinogenesis," *Journ. of the Natl. Cancer Institute*, 56[6]:1237–1242 (1976).

(List continued on next page.)

*Primary Examiner*—Jerome D. Goldberg
*Attorney, Agent, or Firm*—Quarles & Brady

[57] ABSTRACT

A method of causing carcinoma regression is disclosed. One administers an effective amount of perillic acid methyl ester. The use of perillic acid methyl ester is disclosed. A pharmaceutical composition involving perillic acid methyl ester is disclosed.

3 Claims, 15 Drawing Sheets

OTHER PUBLICATIONS

Homburger, et al., "Inhibition Of Murine Subcutaneous And Intraveneous Benzo(rst)pentaphene Carcinogenesis By Sweet Orange Oils and D–Limonene," *Oncology,* 25:1–10 (1971).

Stampfer, "Isolation And Growth Of Human Mammary Epithelial Cells," *Journ. of Tissue Culture Methods,* 9[2]:107–115 (1985).

Hammond, et al., "Serum–Free Growth Of Human Mammary Epithelial Cells: Rapid Clonal Growth In Defined Medium And Extended Serial Passage With Pituitary Extract," *Proc. Natl. Acad Sci. USA,* 81:5435–5439 (1984).

Stampfer, et al., "Induction Of Transformation And Continuous Cell Lines From Normal Human Mammary Epithelial Cells After Exposure To Benzo[a]pyrene," *Proc. Natl. Acad. Sci. USA,* 82:2394–2398 (1985).

Eldridge, et al., "Association Of Decreased Intercellular Communication With The Immoral But Not The Tumorigenic Phenotype In Human Mammary Epithelial Cells," *Cancer Research,* 49:4326–4331, (1989).

Schmidt, et al., "Evidence For Post–Translational Incorporation Of A Product Of Mavalonic Acid Into Swiss 3T3 Cell Proteins," *Journ. of Biol. Chem.,* 259[16]:10175–10180 (1984).

Laemmli, U.K., "Cleavage Of Structural Proteins During The Assembly Of The Head Of Bacteriophage T4," *Nature,* 227:660–685 (1970).

Laskey, et al., "Protein Measurement With The Folin Phenol Reagent," *J. Biol. Chem.,* 193:265–275 (1951).

Crowell, et al., "Selective Inhibition Of Isoprenylation Of 21–26kDa Protein By The Anticarcinogen d–Limonene And Its Metabolites," *The Journ. of Biol. Chem.,* 266[26]:176–9–17685, (Sep., 1991).

Gould, "Chemoprevention And Treatment Of Experimental Mammary Cancers By Limonene," *Proc. of the Amer. Assoc. For Cancer Res.,* 32:474–475 (Apr. 11, 1991).

Gibbs, J. B., "Ras C–Terminal Processing Enzymes–New Drug Targets," *Cell,* 65:1–4 (1991).

Haag, et al., "Enhanced inhibition of protein isoprenylation and tumor growth by perillyl alcohol, an hydroxylated analog of d–limonene," *Proc. Annu. Meet. Am. Assoc. Cancer Res.* 33:524, 1992.

Crowell, et al., "Human metabolism of oral administered d–limonene," *Proc. Annu. Meet. Am. Assoc. Cancer Res.* 33:524, 1992.

Seiyaku, "Novel Antiallergic Agent," Patent abstracts of Japan, 5 (8):C–39 [680], 1981.

Bronfen, et al., "Inhibition of human pancreatic carcinoma cell proliferation by perillyl alcohol," *Proc. Annu. Meet. Am. Assoc. Cancer Res.* 35:431, 1994.

C, NO MONOTERPENE CONTROL
5PA, 5mM PERILLIC ACID
1POH, 1mM PERILLYL ALCOHOL
3POH, 3mM PERILLYL ALCOHOL
EQUAL AMOUNTS OF TOTAL CELLULAR PROTEIN WERE LOADED ONTO EACH LANE OF THE GEL.

USES OF PERILLIC ACID METHYL ESTER

GRANT INFORMATION

This invention was made with United States government support awarded by the National Institute of Health (NIH), Grant #CA38128. The United States Government has certain rights in this invention. This application is a continuation-in-part of U.S. Ser. No 07/865 561 filed Apr. 9, 1992

TECHNICAL FIELD

The present invention relates to uses of perillyl alcohol and perillic acid methyl ester. In particular, the present invention relates to the use of perillyl alcohol and perillic acid methyl ester to reduce serum cholesterol levels, inhibit carcinoma formation and cause carcinoma regression.

BACKGROUND

Limonene is a monoterpene that is present in orange peel oil and has been reported to have activity against mammary (Elegbede, et al., 1984, Carcinogenesis 5:661–664; Elegbede, et al., 1986, J. Natl. Cancer Inst. 76:323–325; Haag, et al., 1991, Proc. Am. Assoc. Cancer Res. 32:402; Elson, et al., 1988, Carcinogenesis 9:331–332; Maltzman, et al., 1989, Carcinogenesis 10:781–783), lung, and stomach (Wattenberg, et al., 1991, Carcinogenesis 12:115–117) cancers. Limonene has also been shown to inhibit certain skin tumors. Van Duuren, et al., 1976, J. Natl. Cancer Inst., 56:1237–1242; F. Homburger et al., 1971, Oncology, 25:1–20.

Although studies have shown that limonene is not toxic to humans at the required usage levels, treatment with limonene is not without some side-effects, particularly when a large dose of limonene is required in a short period.

SUMMARY OF THE INVENTION

In one aspect, the present invention provides a method of causing the regression of carcinomas or the inhibition of carcinoma development. In general terms, the present invention relates to the use of oxygenated monoterpenes to inhibit carcinoma formation and regression and reduce cholesterol levels. Preferred compounds for these purposes are perillyl alcohol and perillic acid methyl ester.

In one embodiment, this method comprises the step of causing the serum level of a mammalian host to reach at least 0.06 mM perillic acid methyl ester.

The present invention is also a method of reducing the serum LDL cholesterol level of a mammal. This method comprises the step of administering an effective amount of perillyl alcohol or perillic acid methyl ester to the mammal, wherein the serum LDL cholesterol level is reduced.

The present invention is also the use of perillic acid methyl ester in the treatment of carcinomas.

The present invention is also the use of perillyl alcohol in the preparation of a formulation for the prevention or inhibition of the formation of carcinomas in a human.

The present invention is also the use of perillyl alcohol in the preparation of a formulation for reducing cholesterol levels in a human.

The present invention is also a pharmaceutical composition for human use which comprises perillic acid methyl ester and a pharmaceutically acceptable carrier.

The present invention is also a pharmaceutical composition for human use which comprises perillyl alcohol together with a vegetable oil.

It is an object of the present invention to reduce serum cholesterol levels.

It is another object of the present invention to inhibit the formation of carcinomas.

It is another object of the present invention to regress carcinomas.

It is another object of the present invention to achieve these goals by creating a serum level of 0.06 mM perillic acid methyl ester.

It is another object of the present invention to provide a pharmaceutical composition of perillyl alcohol together with a vegetable oil.

It is another object of the present invention to provide a pharmaceutical composition of perillic acid methyl ester.

Other objects, features and advantages of the present invention will become apparent after review of the specifications, drawings and claims.

BRIEF DESCRIPTION OF THE PREFERRED EMBODIMENTS

SPECIFIC EXAMPLES

Figure 1:
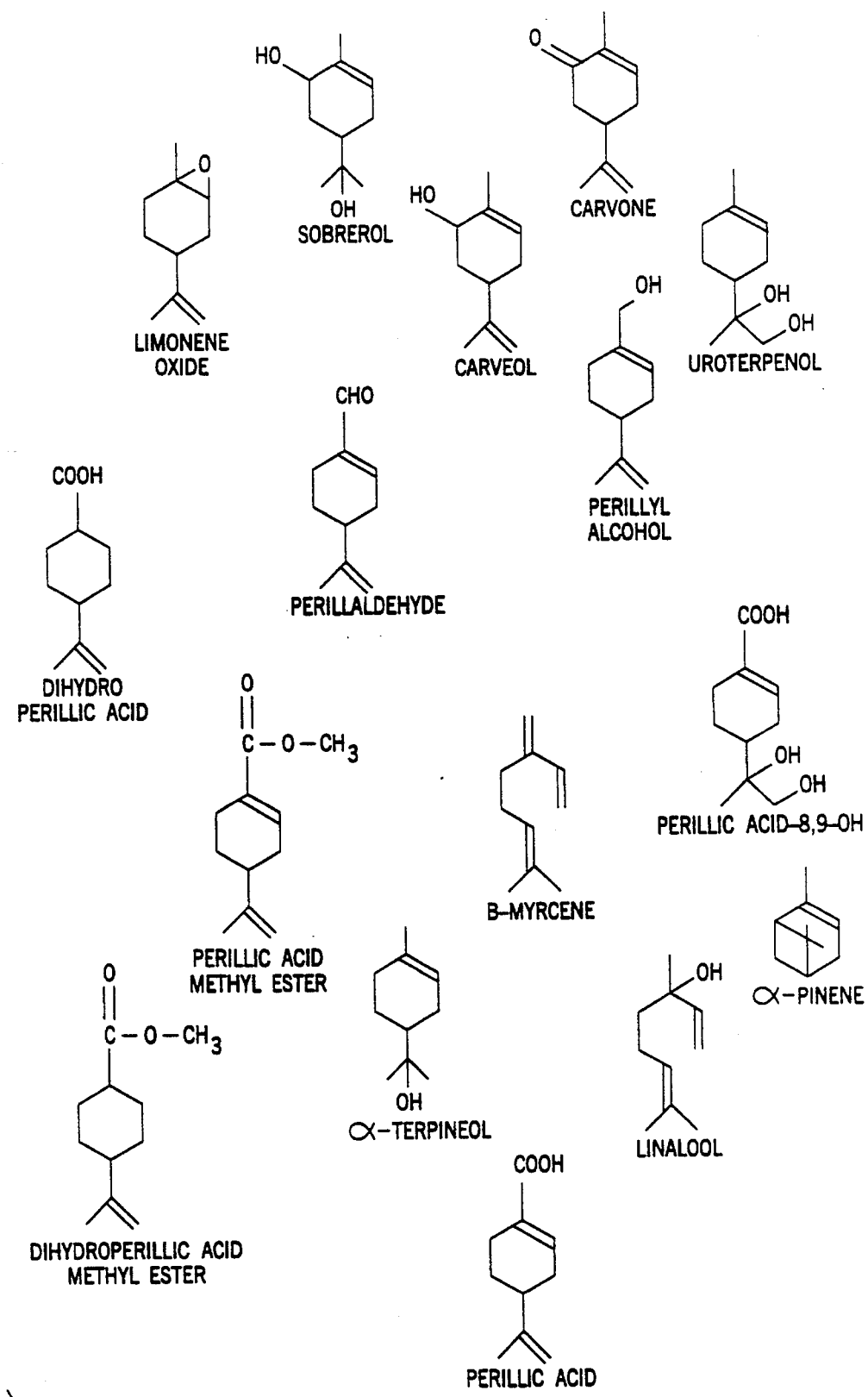
FIG. 1 is a diagram of the chemical structure of 16 terpenes (monoterpenes)

1. Biological Activity a. Cell Culture and Strains

NIH3T3 (mouse embryo) cells were obtained from the American Type Culture Collection and were grown in Dulbecco's modified Eagle's medium supplemented with 10% calf serum. M600B immortalized human mammary epithelial cells (Stampfer, M.R., 1985, J. Tissue Culture Methods 9:107–115) were, obtained from Dr. Martha Stampfer and were grown in supplemented HCDB 170 medium (Hammond, et al. (1984) Proc. Natl. Acad. Sci U.S.A. 81:5435–5439), as described previously (Stampfer, et al. (1985) Proc. Natl. Acad. Sci U.S.A. 82:2394–2398; Eldridge, et al. (1989) Cancer Res. 49:4326–4331).

All cells were maintained in 100-mm dishes at 37° C. in a humidified 5% $CO_2$ atmosphere. Viable cells were distinguished from nonviable cells by counting azure II/methylene blue-stained colonies 10 days after the cells were plated at a density of 100 cells per dish. Trypan blue exclusion was measured by incubating cells for 1 min with one drop of trypan blue per 10 ml of cells. Viable (colorless) and nonviable (blue) cells were then counted on a hemocytometer.

b. Measurement of Protein Isoprenylation

"Isoprenylation" is the addition of a multiple of the 5 carbon isoprene unit to a protein. Our experiments in isoprenylation are reported at Crowell, et al. 1991, *J. Biol. Chem.* 266:17679–17685. To test whether a specific monoterpene affects isoprenylation of proteins in cells, cell extracts were incubated with a radioactive isoprene precursor and 0–5 mM of the test monoterpene and then subjected to SDS-PAGE. Because they carried a radioactive label, isoprenylated proteins were visualized by fluorography. As a control, cells were incubated without the monoterpene.

Isoprenylation of proteins was measured essentially as described by Schmidt, et al., 1984, *J. Biol. Chem.* 259:10175–10180. In brief, cells were treated with 30 µM lovastatin for 24 hours and then incubated for 3 hours in fresh medium containing 15 µCi/mL (R,S) - $[2-^{14}C]$ mevalonolactone (50 mCi/mmol), 30 µM lovastatin, and, where indicated, a test monoterpene. For both isoprenylation and cell growth assays, the monoterpenes were mixed with prewarmed (37° C.) medium containing 10% calf serum, and then the monoterpene-containing medium was added to cells. The relative effects of various monoterpenes on protein isoprenylation were compared by comparison of the relative intensity of bands on fluorograms from $[^{14}C]$-mevalonate-labelled cells treated with each monoterpene. 10% calf serum was included in the normally serum-free HCDB 170 medium of control and limonene-treated M600B cells during the 3 hours incubation to solubilize limonene.

Cells were harvested after trypsin treatment, washed twice with phosphate-buffered saline, suspended in electrophoresis sample buffer (Laemmli, U.K., 1970, *Nature* 227:680–685), and either analyzed immediately or stored at −20° C. Whole cell extracts were analyzed by SDS-PAGE on 16-cm×18-cm×0.75-mm gels by the method of Laemmli (supra). The acrylamide concentrations were 5% for the stacking gel and 12% for the separating gel. Gels were stained with Coomassie Brilliant Blue, equilibrated for 20 min in Amplify (Amersham Corp.) fluorographic reagent, dried under vacuum at 65° C., and exposed to preflashed Kodak X-Omat AR film as described by Laskey and Mills (1975, *Eur. J. Biochem,* 56:335–341). Some fluorograms were analyzed further by densitometry. Where indicated, gels were sliced, dissolved at 50° C. for 3 hours in 0.5 ml of water+0.5 ml of Solvable (Amersham), and then analyzed by scintillation spectrometry in 10 ml of Atom light (Amersham) mixture. Protein content was measured by the method of Lowry, et al. (1951, *J. Biol. Chem.* 193:265–275).

As reported in Crowell, et al., 1991 (supra) radioactivity derived from $[2-^{14}C]$mevalonolactone was detected in control cells in bands corresponding to molecular masses of 66, 46, 21–26, and 17 kDa, as well as at the dye front. Cells treated with 0.5 mM or 5 mM limonene exhibited a dose-responsive decrease in intensity of the 21–26-kDa bands. The spot at the dye front was reduced with maximal inhibition at 5 mM (the limit of solubility). The intensity of the 66-, 46-, and 17-kDa bands from the limonene-treated cells was not different from that of the control. Slicing and scintillation counting of a duplicate gel revealed that limonene inhibited isoprenylation of the 21–26-kDa bands to ~50% of the control at 0.5 mM and ~25% of the control at 5 mM.

c. Test Panel of Monoterpenes in NIH3T3 Cells

The monoterpenes listed in Table 1 (hereafter) and other FIG. 1 compounds were analyzed as described above for their ability to differentially inhibit isoprenylation in NIH3T3 (mouse embryo) cells. FIG. 1 depicts the structures of certain monoterpenes. Limonene was tested at a concentration of 5 mM; all other terpenes were tested at a concentration of 1 mM.

The degree of isoprenylation was evaluated by the amount of labeled protein present in the 21–26 kDa range, as evidenced by fluorography. These results were quantitated according to the intensity of the radioactive image. The monoterpenes differentially inhibited isoprenylation. Of the test panel, perillyl alcohol demonstrated the greatest ability to inhibit isoprenylation.

d. Inhibition of Protein Isoprenylation in M600B Human Cells

The ability of limonene to inhibit isoprenylation of proteins was tested in the immortalized human mammary epithelial cell line M600B. Protein isoprenylation in the absence and presence of 5 mM limonene was measured under identical conditions in NIH3T3 and M600B cells. Samples from each cell line were then analyzed on the same gel. The control mammary epithelial cells exhibited the ability to isoprenylate proteins of 23–26 kDa. Other bands, corresponding to molecular masses of 72, 66, 46, and 17 kDa, could be detected in the mammary epithelial cells after longer exposures. The intensity of the 21–26 kDa bands from untreated cells was much greater for the mammary epithelial cell line than the NIH3T3 cell line.

As in the NIH3T3 cells, M600B cells treated with 5 mM limonene exhibited a marked decrease in the intensity of the 21–26 kDa bands. The effect was dose responsive, with at least 1 mM limonene required for significant inhibition of protein isoprenylation.

Figure 2:
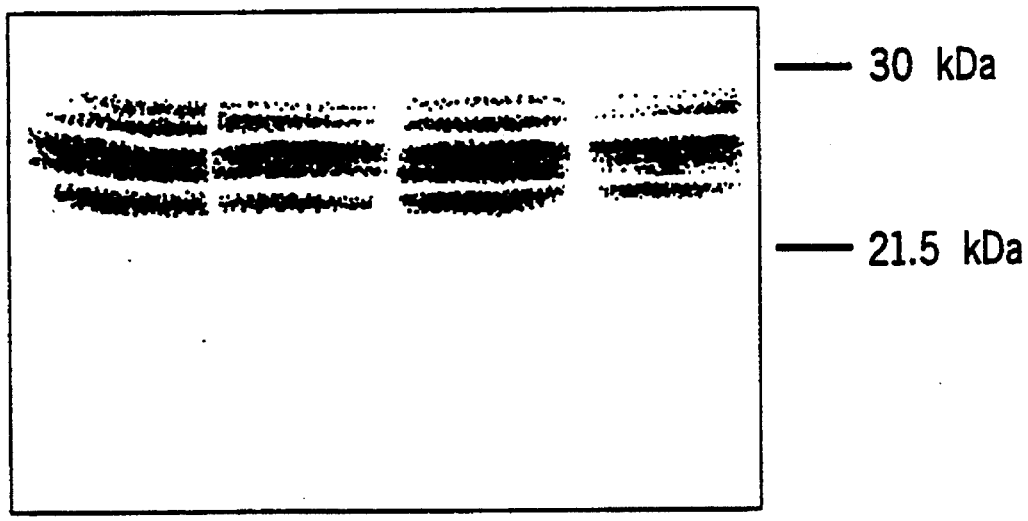
FIG. 2 is a fluorogram revealing the effects of perillic acid and perillyl alcohol on isoprenylation of proteins in M600B human cells.

As in NIH3T3 cells., isoprenylation of 21–26 kDa proteins in M600B human mammary epithelial cells was inhibited significantly by 3 mM perillyl alcohol and 5 mM perillic acid. FIG. 2 is a copy of a fluorogram that demonstrates these results. This experiment also illustrated the ability of these methods to detect various degrees of inhibition of protein isoprenylation.

The relative inhibition by terpenes varies slightly between cell types, but in all cases we have examined, inhibition of isoprenylation by perillic acid and perillyl alcohol was observed.

e. Inhibition of Cell Growth

Figure 3:
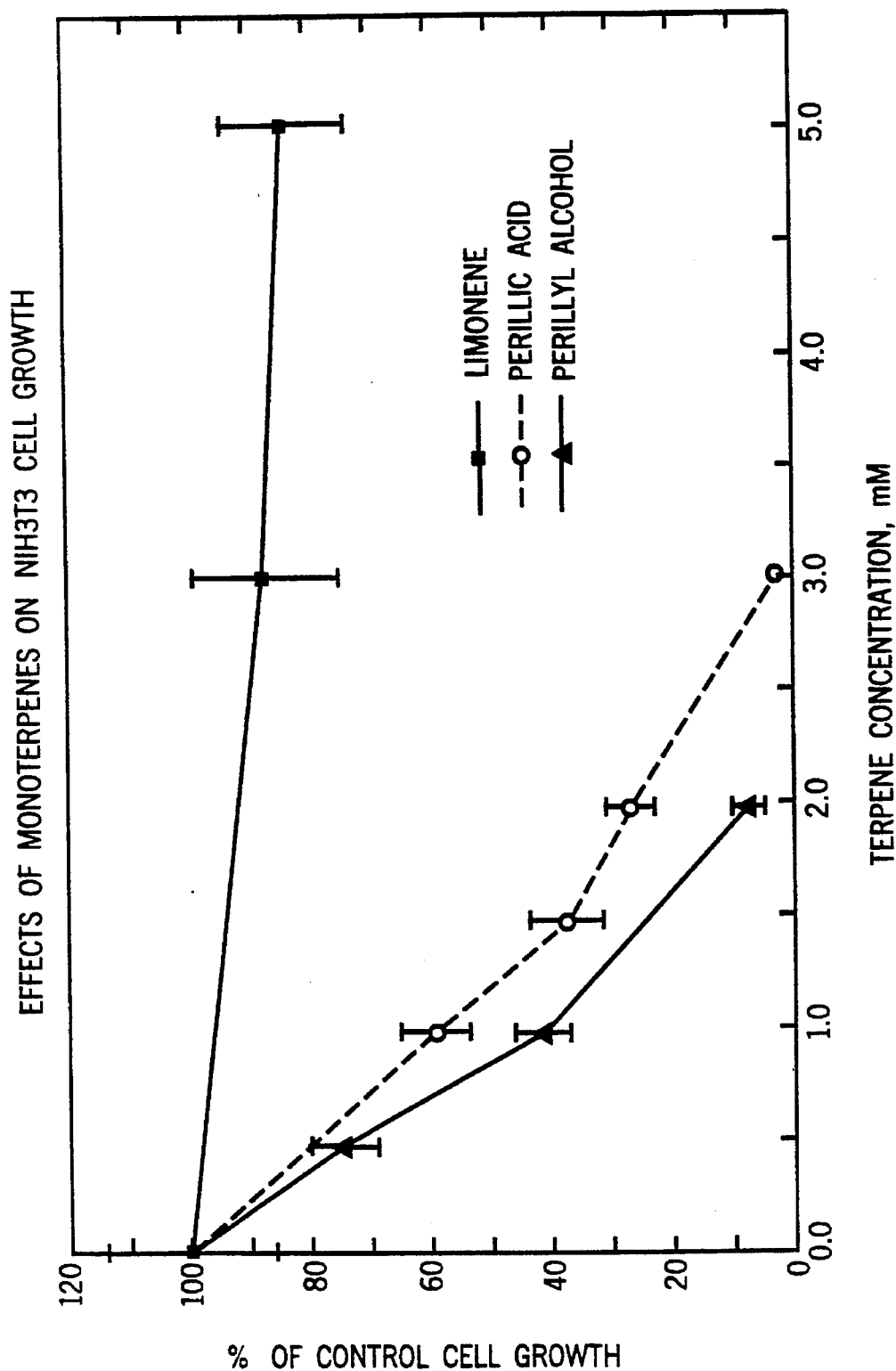
FIG. 3 is a diagram of the effect of limonene, perillic acid and perillyl alcohol on NIH3T3 cell growth.
Figure 4:
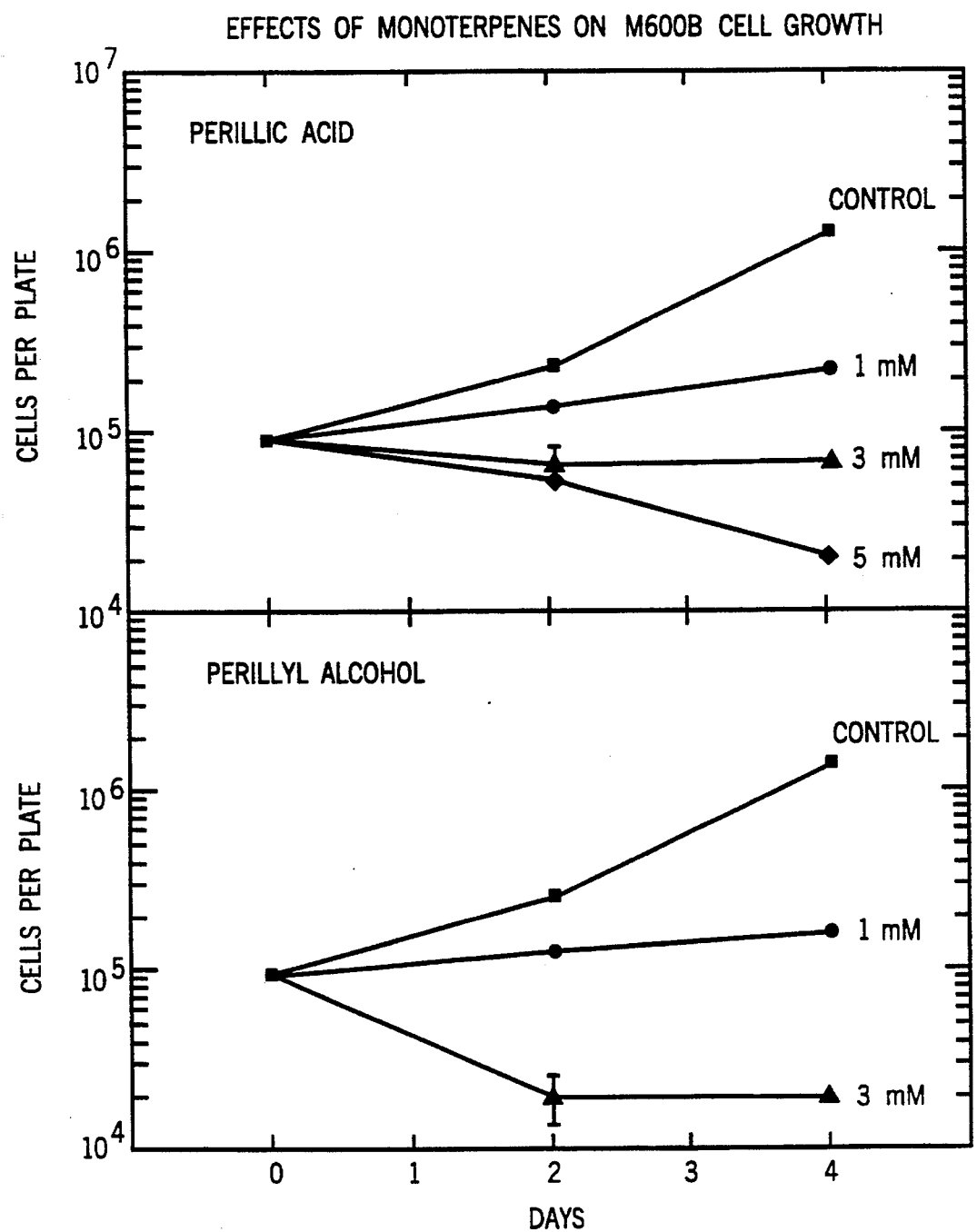
FIG. 4 is a diagram of the effect of perillic acid and perillyl alcohol on M600B cell growth.
Figure 5A:
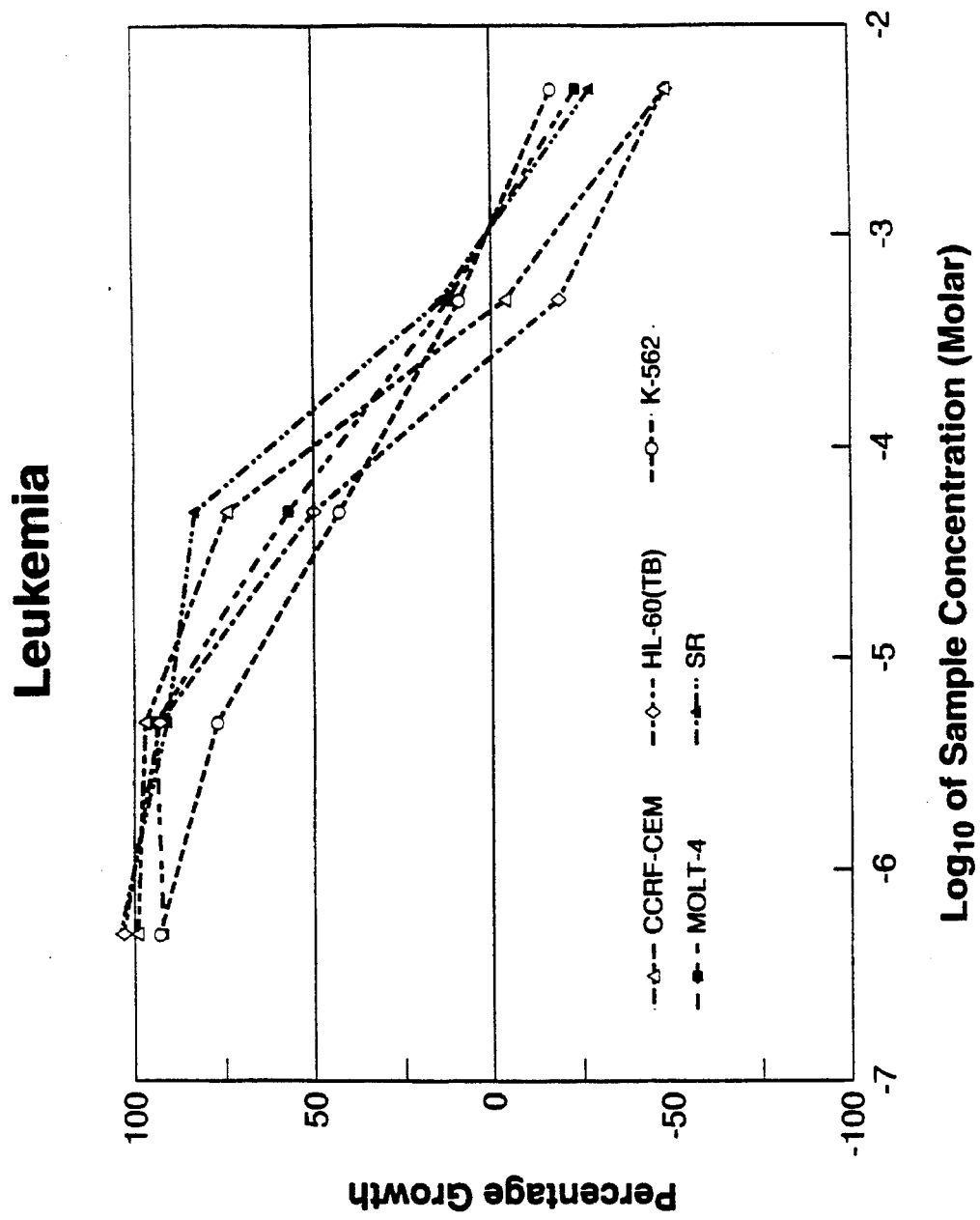
FIGS. 5a–h are a set of diagrams demonstrating the effect on percentage growth of a variety of human cancer cell types of various concentrations of perillyl alcohol.
Figure 5B:
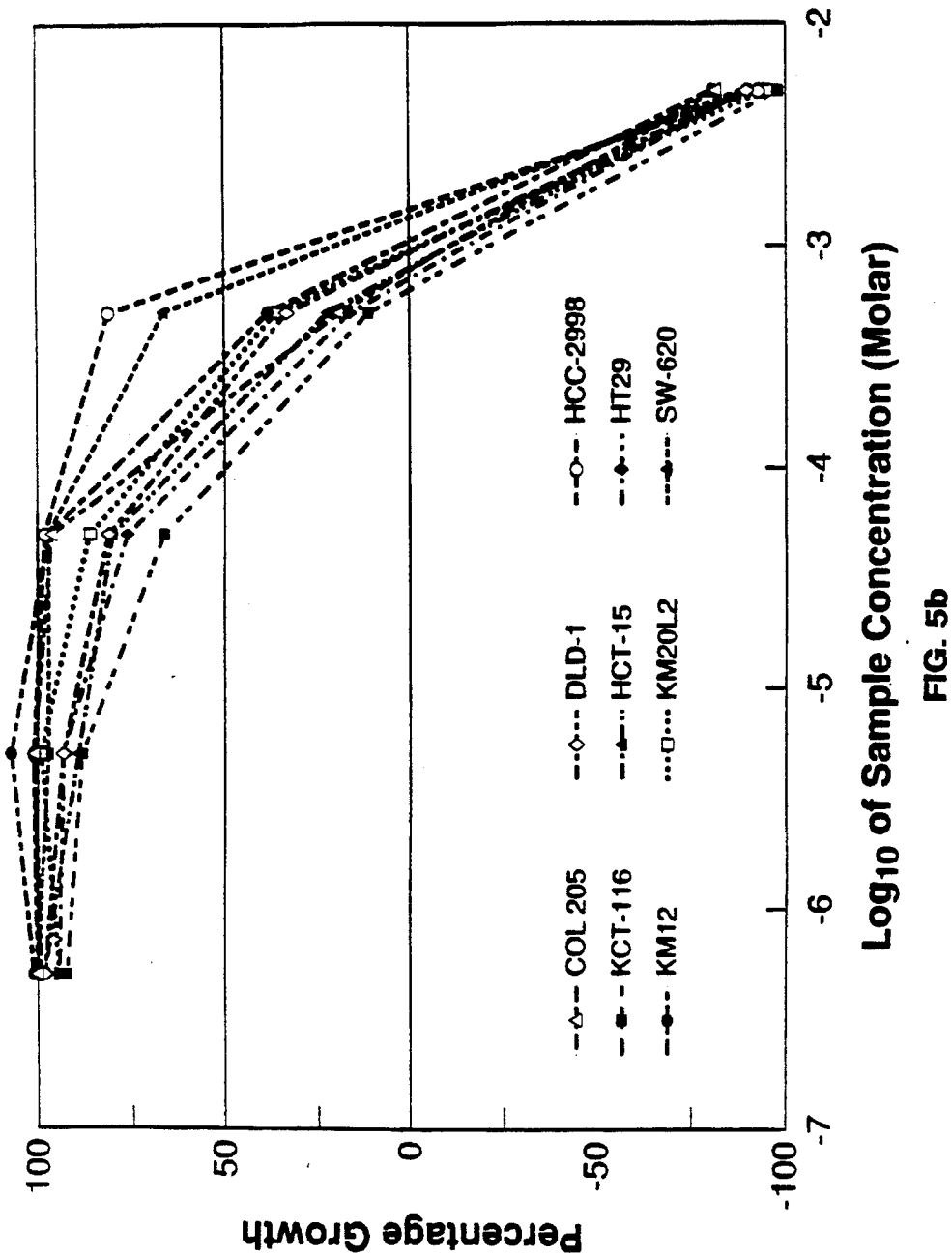
Figure 5C:
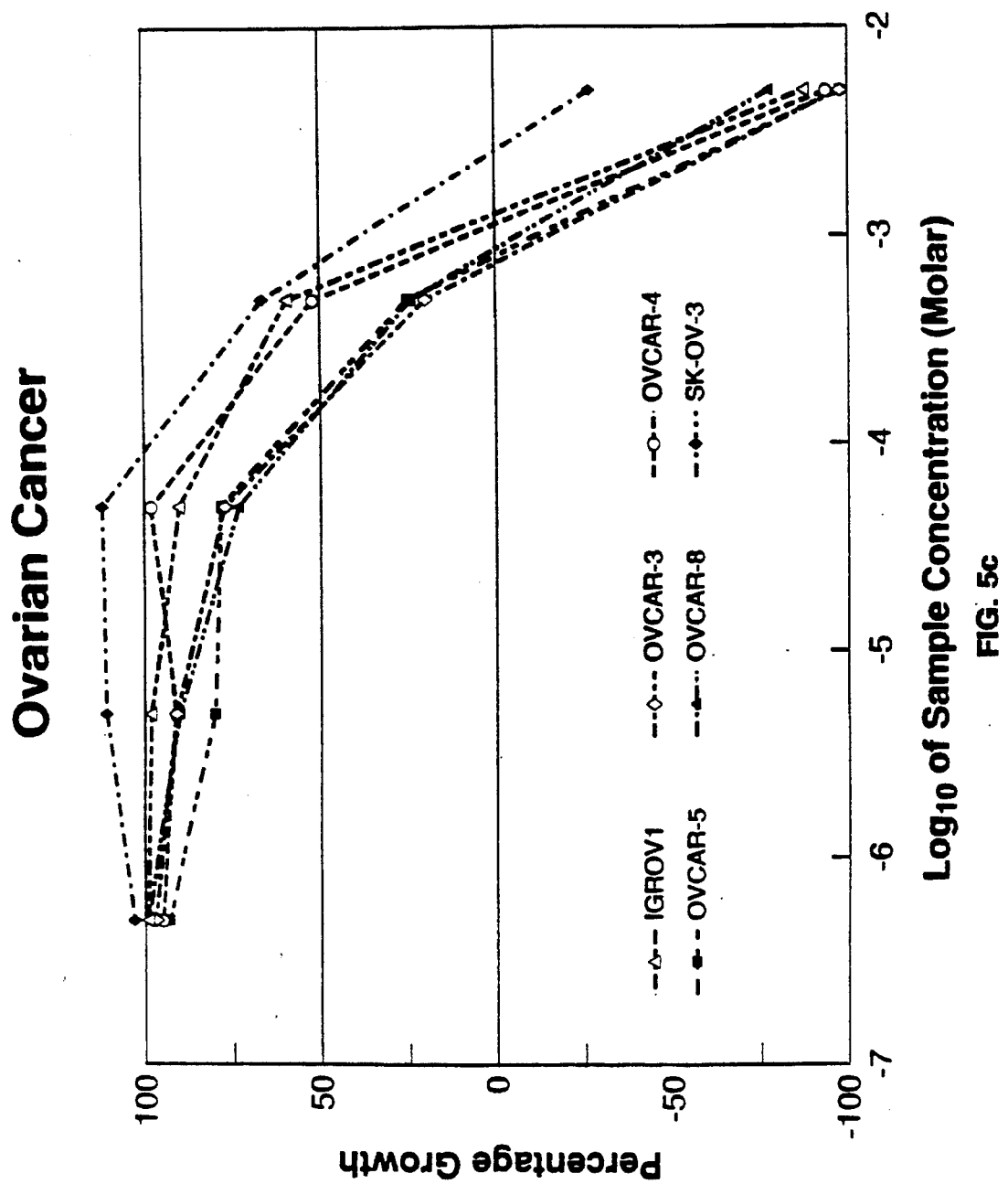
Figure 5D:
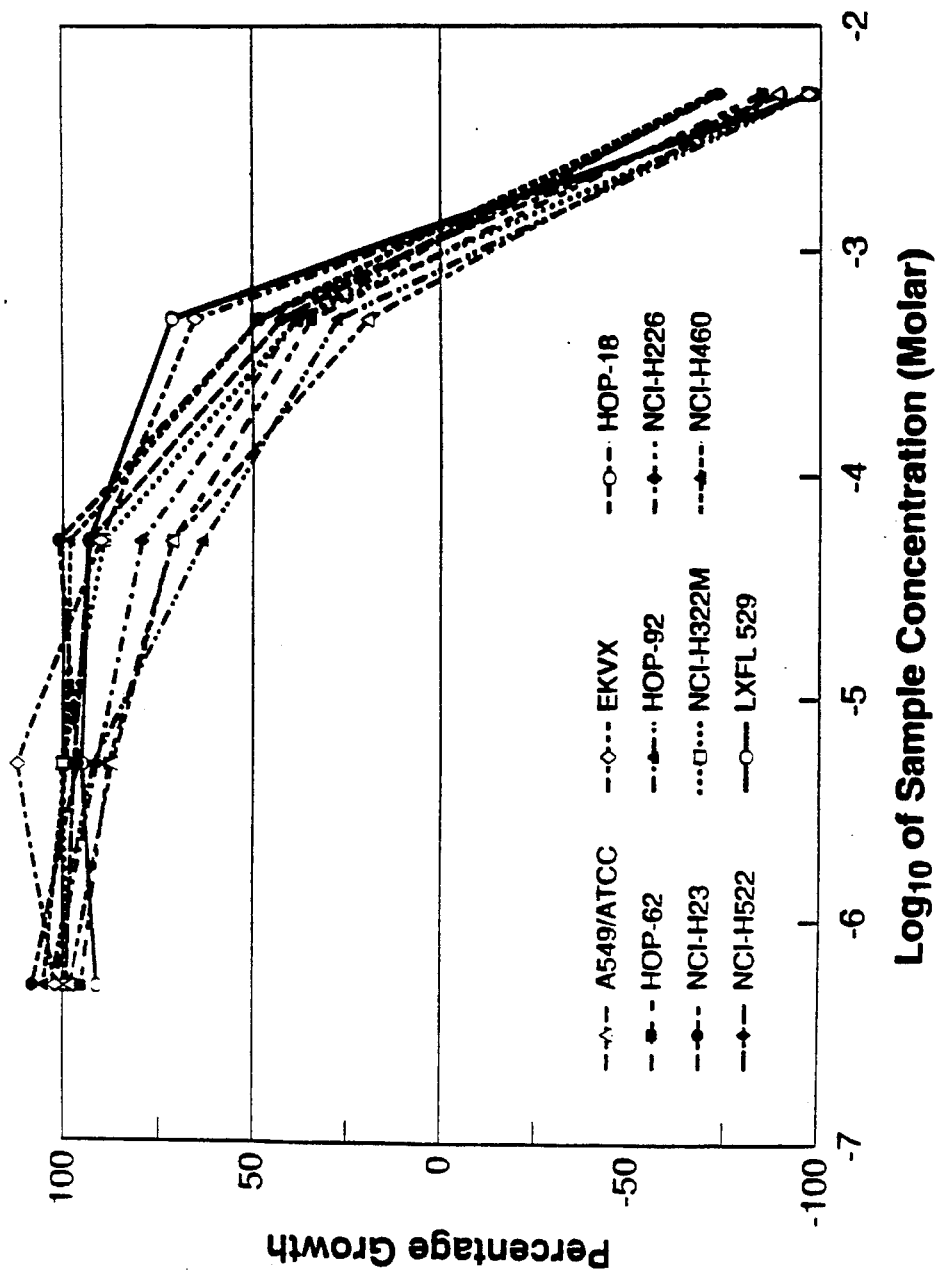
Figure 5E:
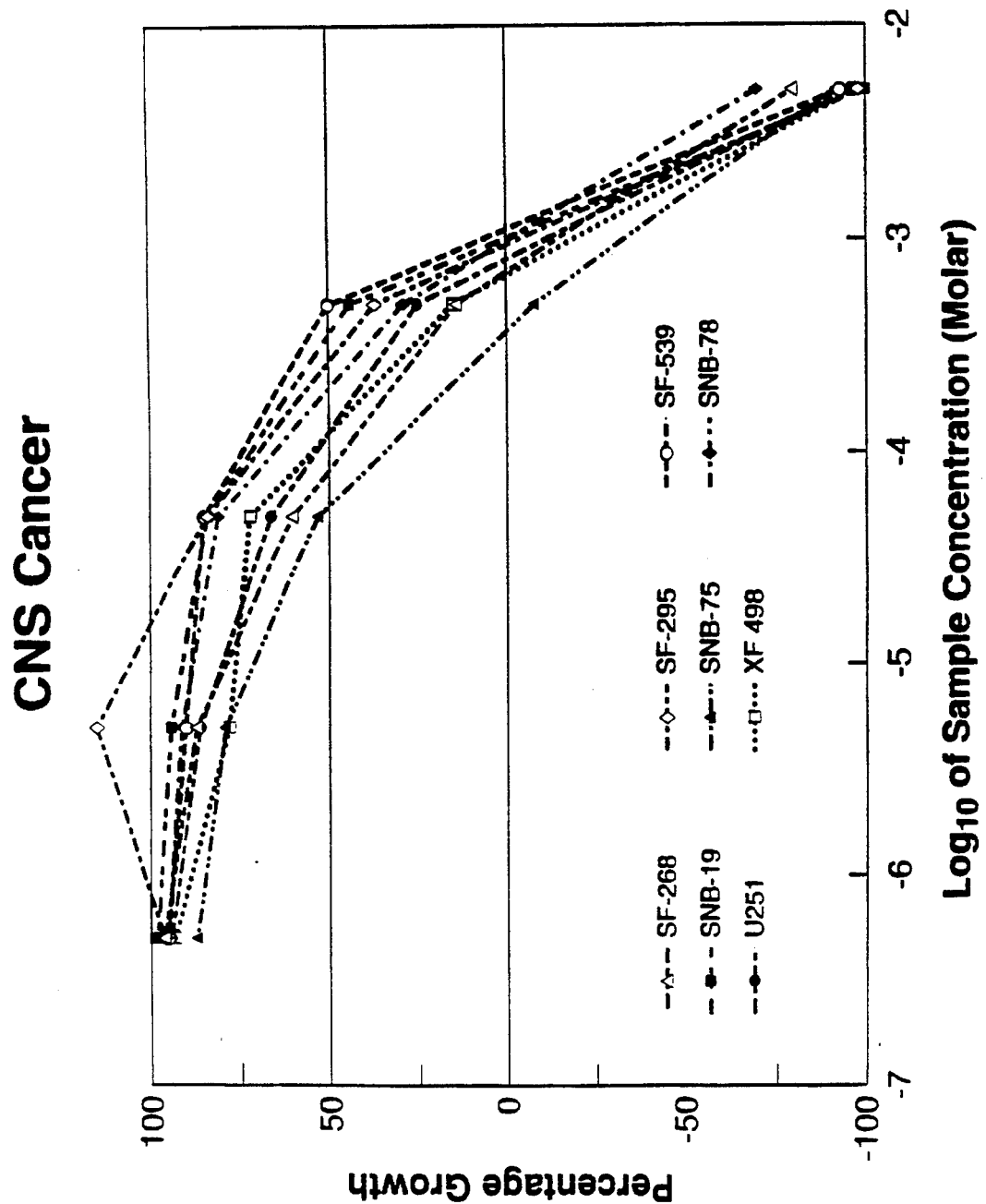
Figure 5F:
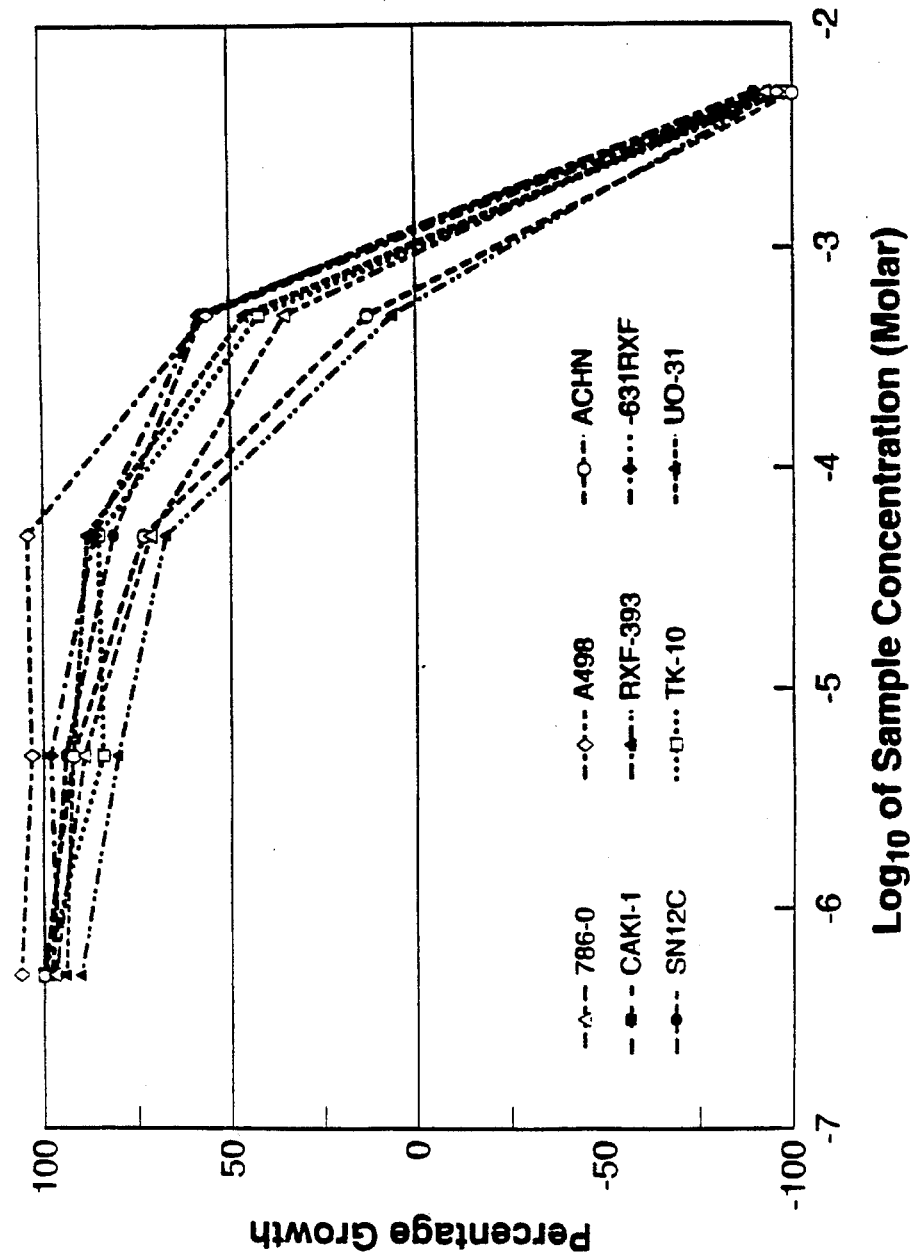
Figure 5G:
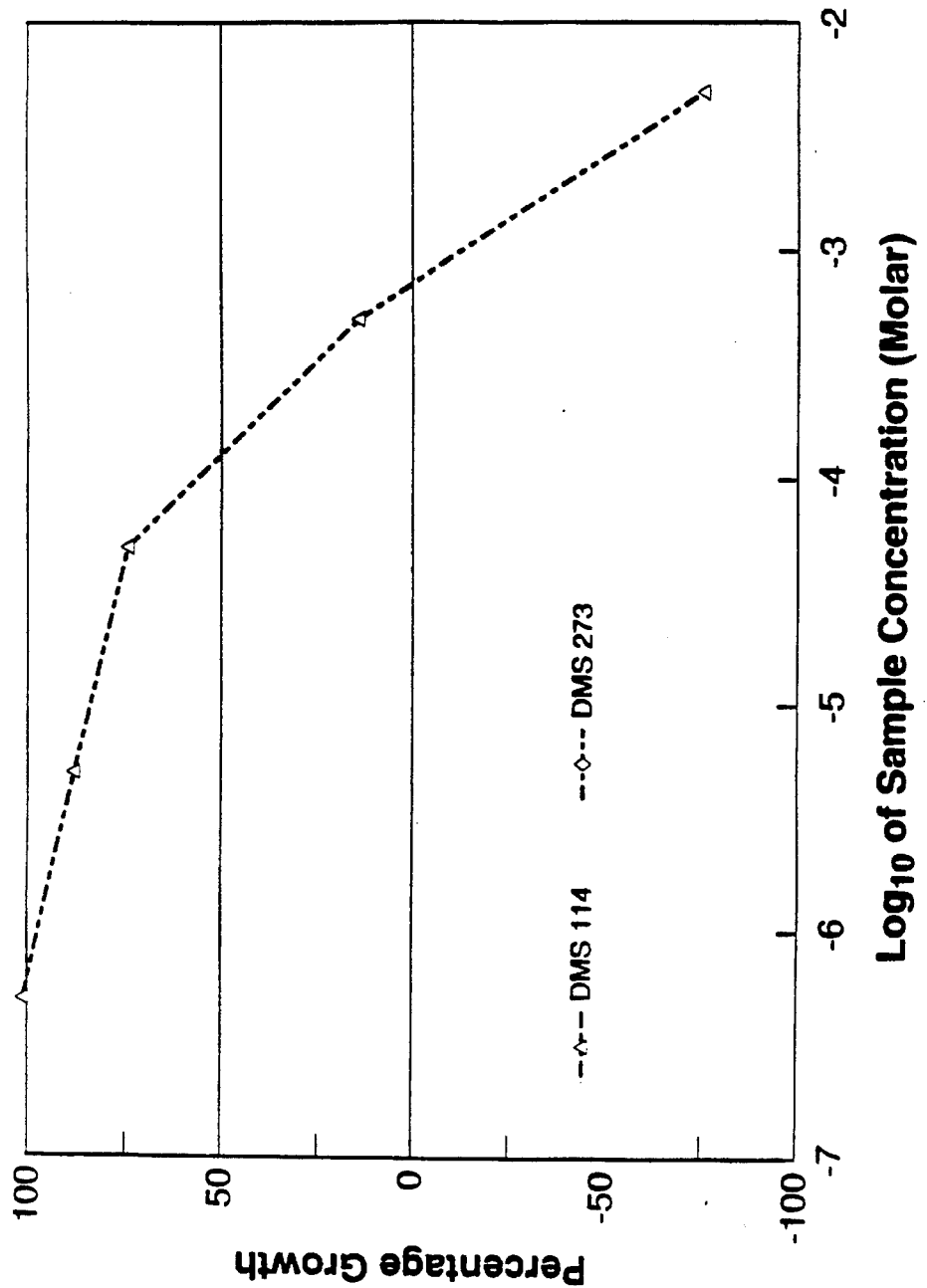
Figure 5H:
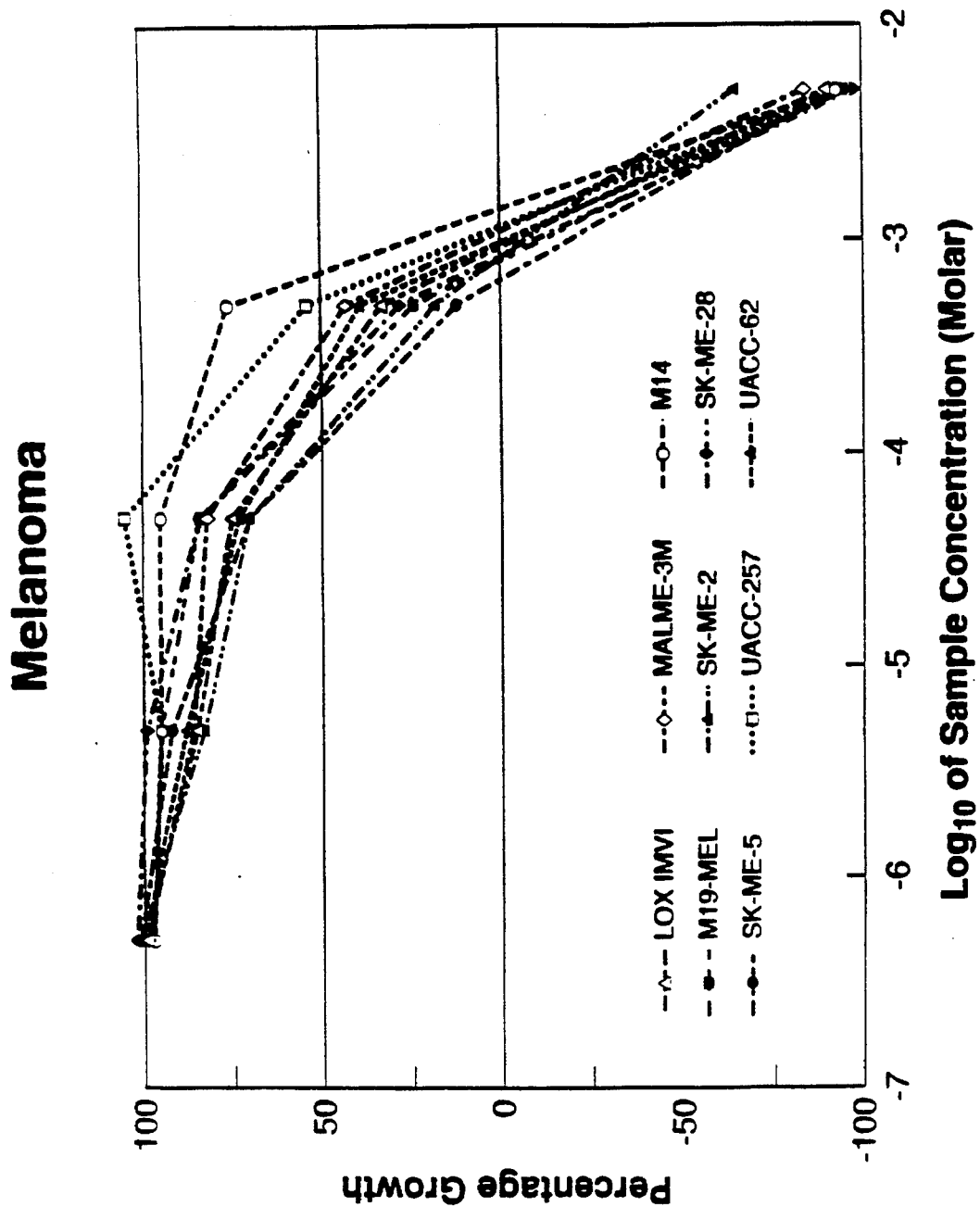

We examined the effect of several of the terpenes on certain types of cell growth. For the human and murine cells, both perillic acid and perillyl alcohol significantly inhibited cell growth in a dose-dependent manner (FIGS. 3 and 4, respectively). Additionally, growth of HT29 (human colon adenocarcinoma) cells was inhibited by 80% by 1 mM perillyl alcohol.

In another experiment, perillic acid methyl ester and perillyl alcohol were the most potent inhibitors of HT29 tumor cell proliferation, each with an $IC_{50}$ value of 50 µM. Table 1 describes the results of that experiment.

TABLE 1

Rank order comparison of cell proliferation inhibition by monoterpenes

| Monoterpene | Rank order* Inhibition of HT-29 tumor cell proliferation |
| --- | --- |
| Perillic acid methyl ester | 1 |
| Perillyl alcohol | 1 |
| Perillylaldehyde | 3 |
| Perillic acid | 4 |
| Limonene | 5 |

*The data are ranked from 1 (greatest inhibition) to 5 (least inhibition). The rank correlation coefficient is calculated to be 0.900, which is significant at the 5% level (Snedecor GW and Cochran WG, Statistical Methods, 1980, Iowa State University Press, pp. 191–192).

Various concentrations of perillyl alcohol caused the regression of a number of human cancer cell lines. FIG. 5 is a set of diagrams showing the effects of perillyl alcohol on different cancer cell lines. These experiments were conducted by the National Cancer Institute Developmental Therapeutics Program. In all cases, perillyl alcohol inhibited cancer cell growth.

2. The Effects of Dietary Perillyl Alcohol on Carcinoma Regression in Wistar-Furth Rats a. Carcinoma Induction We used Wistar-Furth female rats for in vivo studies. Wistar-Furth female rats were obtained from Harlan Sprague-Dawley, Inc., (Madison, Wis.). All rats, arriving at 43–48 days of age, were housed at four rats per cage in wire-bottom metal cages and all were maintained with a light/dark cycle of 12 hours. Rats were provided Teklad Lab blox chow and acidified water ad libitum.

After one week of acclimation, the carcinogen DMBA was administered to the rats, which were 50–55 days old at this point. The DMBA was dissolved in a stock solution of 20 mg DMBA/ml sesame oil, heated and allowed to cool to room temperature before administration. DMBA (Eastman Kodak, Rochester, N.Y.) was given as a single gastric intubation of 50 mg DMBA/kg rat body weight.

b. Monoterpene Administration.

In the pair-feeding study, a group of 70 mammals was treated with DMBA. Beginning four weeks post carcinogen administration, mammals were weighed and palpated weekly. Upon palpation of the first mammary carcinoma (diameter≧3 mm), mammals were randomly assigned to control or 2.5% (w/w) perillyl alcohol diet and pair-fed. In a separate experiment, mammals were assigned control or 10% (w/w) limonene diet and pair fed.

Perillyl alcohol (>96% pure by GC analysis, Aldrich, Milwaukee, Wis.) and Teklad 4% mouse/rat diet meal were thoroughly mixed and stored at −20° C. Fresh diets were made every 7–10 days. All mammals were provided fresh diet daily to minimize evaporation of the monoterpenes. For pair-feeding, the quantity of diet consumed by the monoterpene-fed mammals was measured every 24 hours and the assigned partner was pair-fed accordingly.

c. Carcinoma Regression Evaluation

In the pair-feeding study, all palpable mammary carcinomas were classified as either "primary" tumors (i.e, the first tumor(s) palpated with a minimum diameter of 3 mm) or "secondary" tumors (i.e. a palpable tumor arising after initial diet assignment). At diet assignment, some mammals had more than one primary tumor. All carcinogen-exposed mammals not bearing a first palpable tumor by week 15 post-carcinogen were removed from the experiment. Complete regression of a tumor was defined as non-palpability for a minimum of three consecutive weeks. All mammals in the pair-feeding study were followed for a minimum of 10 weeks post-diet assignment for tumor growth or regression at primary tumor sites and all other mammary glands. The rats were necropsied if moribund. Complete necropsies were performed on all rats at the termination of the study. Greater than 95% of tumors remaining at the autopsy date were diagnosed as mammary carcinomas based on gross and histopathological criteria.

d. Results of the Pair-Feeding Study

DMBA-treated mammals were assigned to perillyl alcohol or limonene diet at an average of 10.4 weeks±0.5 (mean± SEM). At the time of diet assignment, the average tumor diameter was 4.4 mm±0.2. Mammals were assigned to the control group 10.1 weeks±0.5 post-DMBA treatment. Their average tumor diameter at diet assignment was 3.9 mm±0.2.

Figure 6:
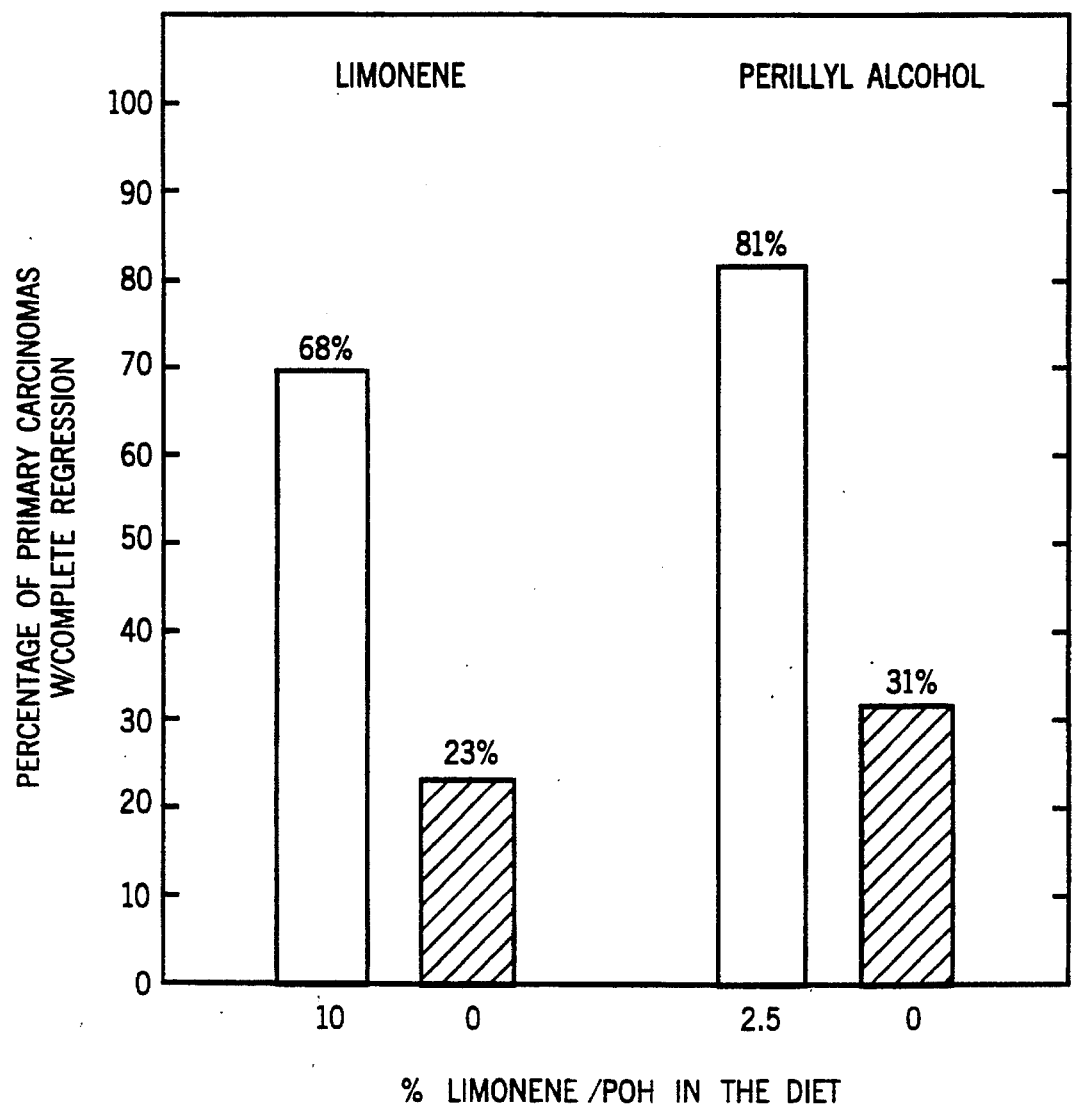
FIG. 6 is a bar graph comparing the effects of a 10 limonene diet and a 2.5% perillyl alcohol diet in the regression of mammary carcinomas.

Table 2 and FIG. 6 disclose the results of these experiments. DMBA-induced primary carcinomas in perillyl alcohol-treated mammals had a complete regression rate of 81% (22 tumors out of 27) compared with 31% (9 tumors out of 29) for pair-fed controls. DMBA-induced primary carcinomas in limonene-treated mammals had a complete regression rate of 68% (19 tumors out of 28) compared with a rate of 23% (6 tumors out of 26) for pair fed controls. We therefore noted that the amount of perillyl alcohol needed to achieve these results was 25% the amount of limonene needed, The time required for a primary carcinoma to regress to a non-palpable mass in the perillyl alcohol-treated group was shorter than the time for spontaneous regression in the pair-fed controls. (3.6 wks±0.3 versus 5.6 wks.±1.1),

TABLE 2

Complete regression of DMBA-induced rat mammary carcinomas by dietary limonene and perillyl alcohol.

| DMBA | Rats (n) | Primary Carcinoma Regression (%) | **Time to Regress (wks) | Number of Secondary Carcinomas/Rat | Secondary Carcinoma Regression (%) |
| --- | --- | --- | --- | --- | --- |
| 10% limonene diet | 25 | *19/28 (68) | *3.25 | *1.08 | *17/27 (63) |
| Pair-fed control | 25 | 6/26 (23) | 14.5 | 1.92 | 9/48 (19) |

TABLE 2-continued

Complete regression of DMBA-induced rat mammary carcinomas by dietary limonene and perillyl alcohol.

| DMBA | Rats (n) | Primary Carcinoma Regression (%) | **Time to Regress (wks) | Number of Secondary Carcinomas/Rat | Secondary Carcinoma Regression (%) |
|---|---|---|---|---|---|
| 2.5% POH diet | 26 | 22/27 (81) | 3.6 ± 0.3 | 0.04 | 0/1 (0) |
| Pair-fed control | 26 | 9/29 (31) | 5.6 ± 1.1 | 1.62 | 11/42 (26) |

*Significantly different than controls ($p < 0.01$).
**Kaplan-Meier estimate of the time when 25% of carcinomas will have regressed.

Figure 7:
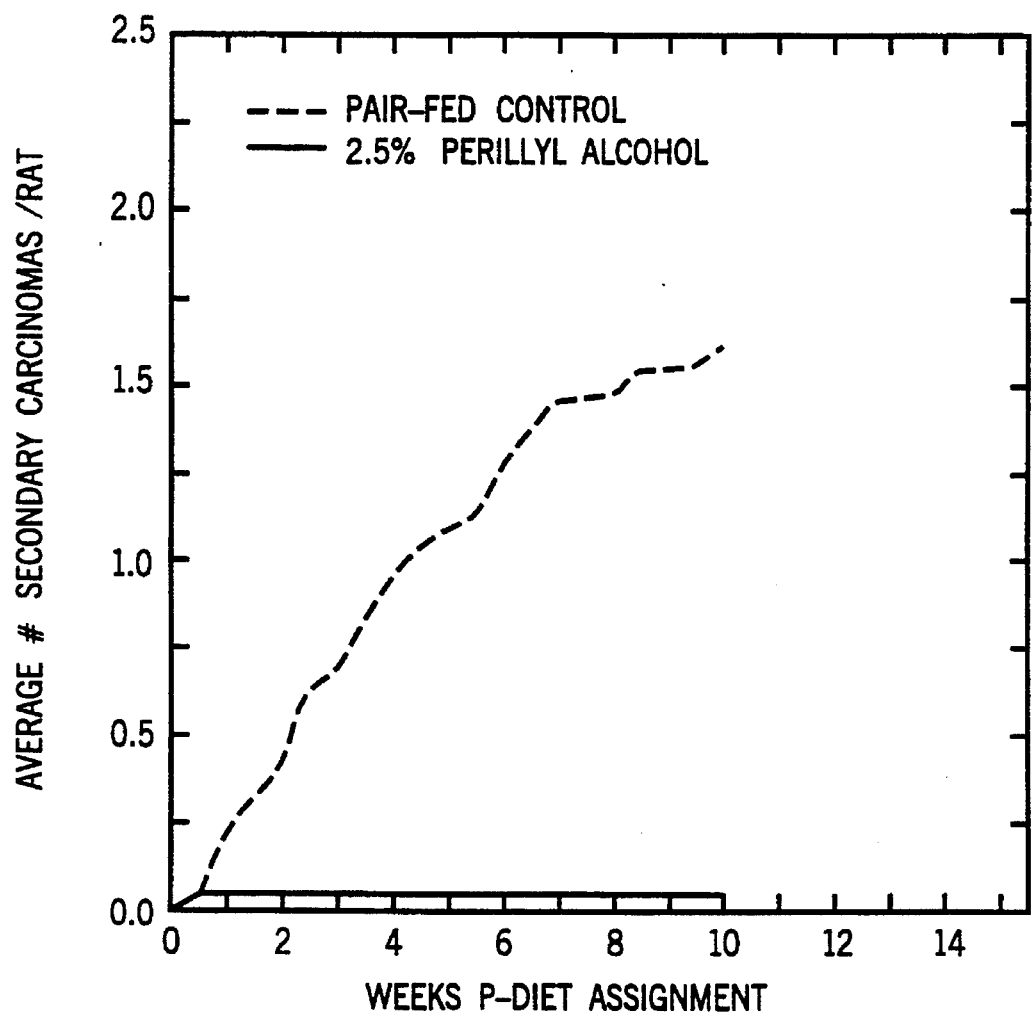
FIG. 7 is a diagram comparing the average number of secondary mammary carcinomas in mammals fed 2.5% perillyl alcohol and in pair-fed controls.

Perillyl alcohol also limited the development of secondary carcinomas arising after initial diet assignment. The average number of secondary carcinomas/mammal for mammals consuming 2.5% perillyl alcohol diet was 0.04 (1/26) as compared to 1.62 (42/26)for pair-fed controls. Table 2 discloses that the number of secondary carcinomas was higher in the limonene-fed mammals than in the mammals that were fed perillyl alcohol. FIG. 7 is a diagram comparing secondary carcinomas in perillyl alcohol-fed animals and controls.

e. Toxicity

Figure 8:
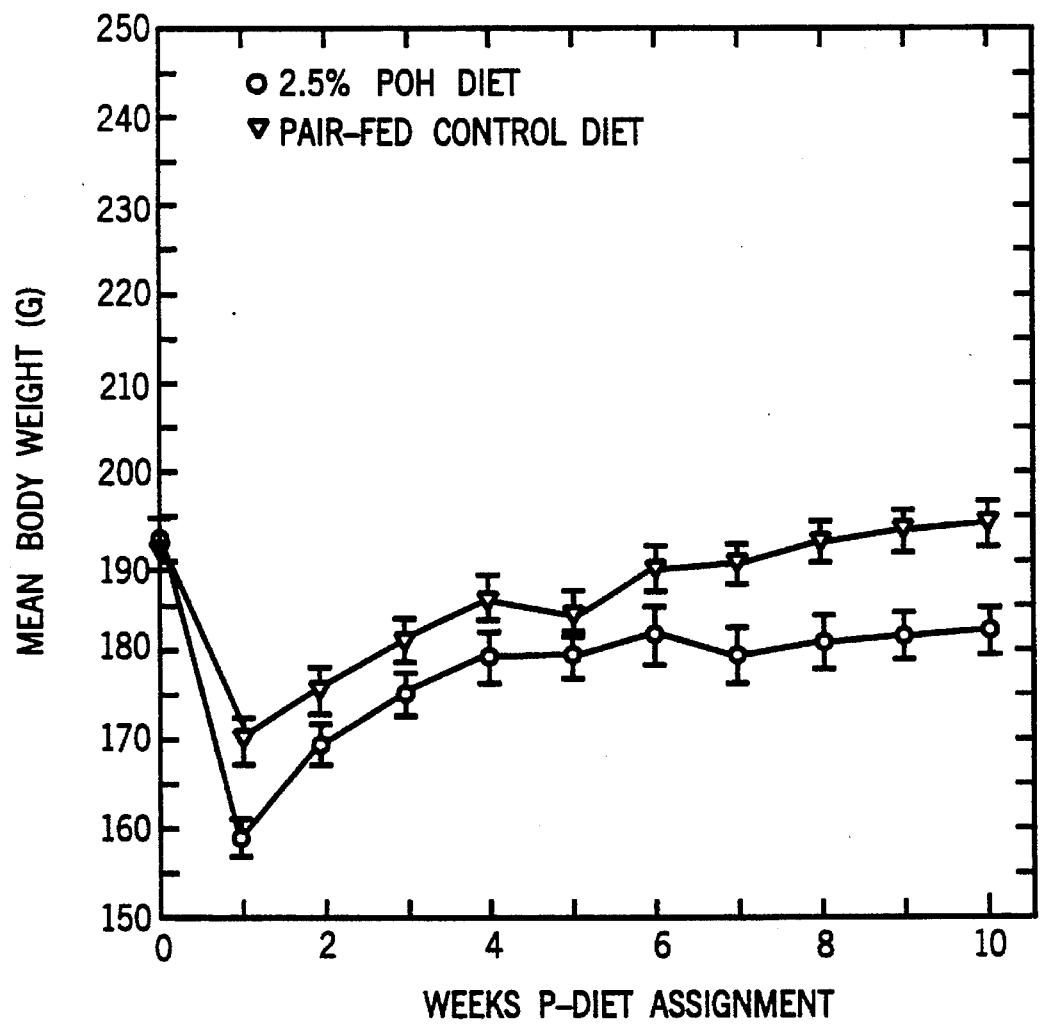
FIG. 8 is a diagram of the effect of perillyl alcohol on mammal weight gain.

Toxicity was limited to weight loss in perillyl alcohol-fed rats. FIG. 8 diagrams these results. Both perillyl alcohol-fed and control mammals experienced initial weight loss followed by weight gain and a plateau. The perillyl alcohol-fed rats did not achieve weights similar to controls. In toxicity studies (data not shown), 2.5% perillyl alcohol diet was the maximum dose tolerated by the animals.

Specifically, the following was observed after perillyl alcohol treatment of 2-month-old WF female rats: When POH was chronically administered to the rat, a 3.0% POH diet caused death (2/5 rats) and a 2.5% POH diet was tolerated with weight loss observed. A 2.0% POH diet was tolerated with weight loss followed by weight gain, and 0.5% and 1.0% POH diets caused very small weight loss followed by weight gain.

When POH was given in an acute manner (a single oral dose, 1:1 mix with sesame oil, for 5 days), the following was observed: After 300 mg total POH dose, 2 out of 5 rats died within 24 hours. After a 200 mg total POH dose, 2 out of 5 rats died within 24 hours. After a 100 mg total POH dose, 5 out of 5 rats tolerated 5 days with weight loss.

3. Use as a Chemotherapeutic a. Other Carcinoma Types

We also have demonstrated differential isoprenylation and regression of cell growth in colon adenocarcinoma cells (HT29) with perillyl alcohol. Also, FIGS. 5a–h demonstrate inhibition of cell growth in a variety of human cancer cell types.

b. Appropriate Dose and Administration

In our in vivo tests, we used a perillyl alcohol dose of approximately 2.5 g/kg mammal weight. Dosage can also be calculated on a surface area basis. Our mammalian in vivo experiment used a surface area dose of approximately 7.5 g/m$^2$. For a human being, this would translate to a dose of approximately 10–15 g/day.

We administered the dose orally. However, other administration modes, such as intravenous administration, would also be appropriate.

In an extension of our work, the National Cancer Institute has studied the effect of perillyl alcohol doses in nude mice using an oral bid ×14 day schedule. At a dose of 1.0 gram/kg/treatment (diluted 1:1 in sesame oil), the mice lost an average of 3 g of body weight at day 10, but the weight loss leveled off. No weight loss was seen at 0.5g/kg/treatment. Perillyl alcohol was also administered in PEG400 at the same dose levels. Lethality was observed in mice treated with the PEG formulation.

4. Perillyl Alcohol Plasma Metabolite Identification

Materials and Methods

In order to identify the circulating plasma metabolites of perillyl alcohol, female Wistar-Furth rats were given a single dose of limonene or perillyl alcohol (1 g/kg) mixed 1:1 (v:v) in sesame oil by oral intubation. Control animals received oil alone. At the chosen time points, rats were anesthetized with ether and blood was collected into heparinized tubes (Heparin (Sigma, Grade II), at 20 mg/ml in 0.9% saline). Plasma was removed following centrifugation and stored at $-20°$ C.

For quantitation of chronic plasma metabolite levels of perillyl alcohol, female WF rats were housed individually and fed fresh diet daily. The afternoon before blood collection, all rats were given approximately 20 grams of the appropriate diet and allowed to eat ad. libitum for 18 hours. Food consumption data was determined the next morning and the rats were bled within 2 hours following food removal.

Perillyl alcohol, limonene and their metabolites were extracted from plasma by the method of McClean, et al., Clin. Chem. 28:693,1982. Briefly, 5 µl of a 10 mM solution of perillaldehyde was added to 50 µl plasma as an internal standard for quantitation. The plasma was mixed with an equal volume of n-butanol:acetonitrile (1:1, v/v), after which another volume of saturated potassium phosphate was added. After vortexing, the samples were centrifuged and the organic layer removed from the top.

Plasma extracts were analyzed using a Hewlett-Packard 5891 gas chromatograph equipped with a flame-ionization detector or a Hewlett-Packard 5890 chromatograph equipped with a 5971A mass-selective detector, both with 30 m Supelco SPB-5 columns. The temperature program was 90° C. for 4 minutes, increasing by 10° C./minute, followed by 15 minutes at 275° C. The split ratio was 1:10 and the linear velocity was 1.1 ml/minute. Standard curves were generated by adding 5 µl rat plasma. Standards were then extracted and analyzed by capillary gas chromatography. The ratio of the terpene peak area/perillaldehyde peak area versus the concentration of terpene in the sample was plotted. The slope of this line was used to determine the concentration of terpene in the plasma of rats fed perillyl alcohol or limonene.

Results

In order to identify the plasma metabolites of perillyl alcohol, rats were gavaged with an acute dose (1 g/kg) of either limonene or perillyl alcohol, and the plasma was collected at 4 hours post-gavage. The chromatograms of perillyl alcohol-fed rat plasma were compared to those from limonene-fed rats whose metabolites have been previously identified (Crowell, et.al., *Cancer Chemother. Pharmacol.* 31:205, 1992). Identification of the metabolite peaks was made by comparison of retention times of unique peaks in terpene-fed rats to the retention times of synthetic metabolites of limonene. These unique peaks were further identified by comparing the mass spectra of unknowns to those of the synthetic metabolites. The same major limonene metabolites, perillic acid and dihydroperillic acid, were identified as the major plasma metabolites of perillyl alcohol, with minor levels of these acids' methyl esters also present. These same metabolites were found in the plasma of rats chronically fed perillyl alcohol or limonene.

The plasma metabolites in rats acutely or chronically-fed either perillyl alcohol or limonene were then quantitated. The data is summarized in Table 3. Rats chronically fed a 2% perillyl alcohol diet had a 2–3 fold greater total terpene levels when compared to rats fed 10% limonene diet. These dietary levels were chosen because of their abilities to induce similar regression rates in this rat model (Jirtle, et al. *Cancer Research* 53:3849, 1993). Referring to Table 3, the major metabolites of limonene, perillic acid and, dihydroperillic acid, were found at approximately 1:1 ratios for both chronically and acutely limonene-fed rats. In contrast, for perillyl alcohol-fed rats, the ratio of these metabolites was greater than 10:1 in acutely fed rats and greater than 2:1 in chronically fed rats. Neither limonene nor perillyl alcohol was detected in the plasma of chronically fed rats.

These included perillic acid methyl ester.

From acute gavage studies (data not shown), limonene was found in the plasma in acutely fed rats for up to 4 hours and appeared to be metabolized at that time to equal amounts of perillic and dihydroperillic acid. By 24 hours post-administration, no limonene was detectable in the plasma. Thus, we know that metabolite was the active compound.

In contrast, perillyl alcohol was more rapidly converted to metabolites than limonene with perillic acid, being the major metabolite detected. Perillyl alcohol was not detected at any time point including 30 minutes post-gavage, while perillic and dihydroperillic acids were detectable at 24 hours post-administration in rats acutely administered perillyl alcohol. The total plasma terpene levels following an acute administration of perillyl alcohol were 3 times higher than that of limonene at 40 hours post-gavage. These same trends in metabolite levels were found in the chronically fed rats. Rats fed 2% perillyl alcohol diet had total terpene levels approximately 3 times higher than those fed 10% limonene diet. In particular, the ester methyl ester levels developed over time.

It is possible to project the amounts of perillyl alcohol that would be necessary to achieve similar circulating metabolite levels in humans. Rats fed a 1% diet of perillyl alcohol have a regression rate of 55%. We estimate that they consume 0.88 g/kg/day of perillyl alcohol. This converts to 5.2 gm/m$^2$. This gm/m$^2$ dose is the equivalent of approximately 10 g/day for a 70 kg human adult, which is within the acceptable range for human administration. Therefore, a preferred range of dosages of perillyl alcohol is 7.5–15 g/day for a 70 kg human. Most preferably, the dosage is 10 g/day for a 70 kg human. We conclude that the monoterpene perillyl alcohol is an excellent potential candidate for therapeutic trials for human cancers, including those of the breast.

Because perillic acid methyl ester (PAME) is more potent in cell proliferation, tests than perillyl alcohol (See Table 1, supra and see section 8, infra), we believe that perillyl alcohol is an effective prodrug and the methyl ester is the active component. Preferably, the dose range of PAME would be 2–4.5 g/day for a 70 kg human. Most preferably

TABLE 3

Quantitation of the circulating plasma metabolites in rats acutely or chronically fed limonene or perillyl alcohol.

| | # Rats (n) | Treatment | mM LIM/POH[a] (% total) | mM PA (% total) | mM DHPA (% total) | mM PAME (% total) | mM DHPAME (% total) | Total mM |
|---|---|---|---|---|---|---|---|---|
| Acute 4 Hour | 7 | 1 g/kg LIM | 0.09 ± 0.02[b] (13) | 0.27 ± 0.04 (40) | 0.20 ± 0.03 (30) | 0.08 ± 0.01 (12) | 0.03 ± 0.00 (4) | 0.67 |
| | 7 | 1 g/kg POH | 0.00 ± 0.00 (0) | 1.13 ± 0.20 (71) | 0.08 ± 0.01 (5) | 0.38 ± 0.09 (24) | 0.01 ± 0.00 (<1) | 1.60 |
| Chronic Week 3 | 6 | 10% LIM | 0 (0) | 0.10 ± 0.02 (53) | 0.06 ± 0.01 (32) | 0.02 ± 0.01 (11) | 0.01 ± 0.00 (5) | 0.19 |
| | 6 | 2% POH | 0 (0) | 0.40 ± 0.04 (69) | 0.11 ± 0.01 (19) | 0.06 ± 0.01 (10) | 0.01 ± 0.00 (2) | 0.58 |
| Chronic Week 5 | 4 | 10% LIM | 0 (0) | 0.14 ± 0.03 (50) | 0.09 ± 0.02 (32) | 0.04 ± 0.01 (14) | 0.01 ± 0.00 (4) | 0.28 |
| | 4 | 2% POH | 0 (0) | 0.39 ± 0.09 (62) | 0.16 ± 0.02 (25) | 0.06 ± 0.01 (10) | 0.02 ± 0.00 (3) | 0.63 |
| Chronic Week 10 | 10 | 10% LIM | 0 (0) | 0.13 ± 0.01 (48) | 0.12 ± 0.01 (44) | 0.02 ± 0.00 (7) | trace (<1) | 0.27 |
| | 10 | 2% POH | 0 (0) | 0.48 ± 0.04 (59) | 0.23 ± 0.02 (28) | 0.08 ± 0.01 (10) | 0.03 ± 0.00 (4) | 0.82 |

[a]Abbreviations: LIM = limonene; POH = perillyl alcohol; PA = perillic acid; DHPA = dihydroperillic acid; PAME = perillic acid methyl ester; DHPAME = dihydroperillic acid methyl ester.
[b]Mean ± SEM.

As demonstrated above, perillyl alcohol was found to be rapidly metabolized to the same metabolites as limonene.

the dose would be 2.5–3 g/day for a 70 kg human.

5. Metabolism Of Limonene In Humans

In the following section we describe further background relating to our discovery that perillic acid methyl ester is a metabolite of limonene in humans.

Materials and methods

Limonene: Limonene was administered to the human subjects in the form of orange peel oil, which is typically 90–95% d-limonene. The orange oil (Sunkist) used in this study was determined to be 95% limonene by capillary gas chromatography.

Subjects: The subjects were five females and two males, median age of 32 years (range 23–55) and without illness or laboratory abnormalities. All subjects had fasted for 12 hours ! and had refrained from ingesting citrus fruits or citrus-flavored soft drinks for 48 h prior to ingesting the orange oil. Female subjects of child bearing potential had a negative urine pregnancy test on the day of the study.

Administration and evaluation: The subjects ingested 100 mg/kg d-limonene in a semi-solid mixture of custard-like consistency which was 5% (w/w) orange oil. The custard consisted of dry unflavored custard mix, cold water, cold whole milk, and orange oil. The components were blended at room temperature and then refrigerated for at least 30 minutes prior to ingestion by the subjects. Subjects ingested the orange oil-containing mixture over 2–10 minutes. Whole blood was drawn for chemistry panel analysis and for plasma limonene metabolite analysis prior to 0 and 4 h (metabolism analysis only) and 24 h post-ingestion of the orange oil. One subject had additional blood draws for metabolite analysis at 1, 2, and 8 h post-ingestion. The chemistry panel consisted of: BUN, creatinine, calcium, magnesium, phosphorous, uric acid, total cholesterol, total protein, albumin, total bilirubin, y-glutamyl transpeptidase, alkaline phosphatase, aspartate aminotransferase, and lactate dehydrogenase. Subjects were monitored for toxicity for one week.

Gas chromatography of plasma extracts: Limonene metabolism was analyzed in organic extracts of plasma by capillary gas chromatography with on-line flame ionization, mass-selective or infrared detection as described in Crowell, et al., *Cancer Chemoth. and Pharma.* 31:205, 1992. Monoterpene concentrations were determined using the internal standard perillaldehyde as described in Crowell, et al., 1992, supra. Limonene 1,2-diol (p-menth-8-ene-12 diol) was synthesized by the hydrolysis of (+)-limonene oxide (Crowell, et al., 1992, supra.) Perillic acid, dihydroperillic acid, and their methyl esters were synthesized. All other monoterpene standards for gas chromatography were purchased from Aldrich at the highest purity available.

Results

Chemistry panel analysis: No intrasubject changes were observed on the chemistry panel analysis following ingestion of 100 mg/kg d-limonene. No gradeable toxicity was encountered, but the following effects were reported: 4/7 reported mild eructation for 1–4 h post ingestion, 1/7 reported mild satiety for 10 h post-ingestion, and 1/7 noted slight fatigue for 4 h post-ingestion.

Metabolite identification: The presence of limonene metabolites in plasma was assessed by capillary gas chromatography. The flame-ionization chromatograms from 4h post-ingestion time points were first compared to those of the preingestion time point. Several peaks were present in the 4 h chromatograms that are not present in the respective time 0 chromatograms, These peaks were designated H1–H5 in order of retention time. The retention times (Table 4), vapor phase IR spectra (Table 4), and mass spectra were compared to those of the rat plasma limonene metabolites perillic acid, dihydroperillic acid, perillic acid methyl ester, and dihydroperillic acid methyl ester taken from Crowell, et al., 1992, Supra. Four or the five human metabolites had the same retention times (Table 4) and mass spectra (data not shown) as those of rat limonene metabolites, and, where determined, the IR spectra (Table 4) matched as well. On the basis of these criteria, four of the human metabolites were identified as follows: H1=dihydroperillic acid methyl ester, H3=dihydroperillic acid; H4=perillic acid methyl ester, and H5=perillic acid.

One human metabolite, H2, was one of the three most abundant metabolites (along with perillic acid and dihydroperillic acid) in all human subjects. The mass spectrum was somewhat similar to that of two limonene-related diols, p-menth-1-ene-8,9-diol (uroterpenol) and p-menth-1-ene-4,8-diol (sobrerol) (data not shown). Both p-menth-1-ene-1-ene-6,8-diol and metabolite H2 had features typical of terpene alcohols., namely an undetectable molecular ion peak, and prominent peaks of 152 (M+- $H_2O$) and 137 (M+- $H_2O$ and $CH_3$). On that basis, it was hypothesized that metabolite H2 might be an isomer of the two diols listed above. Synthetic limonene-1,2-diol (p-menth1-ene-1,2-diol) was analyzed in the same GC/MS system and found to have the same retention time (Table 4) and mass spectrum as metabolite H2, thus confirming the identity of H2 as limonene-1,2-diol.

In summary, we found that rat metabolism of limonene closely parallels that of humans both in terms of the specific metabolites formed. The concentrations of limonene metabolites were found to be highest at 4 h post-ingestion. By 24 h in all subjects and by 8 h in one more frequently—monitored subject, the concentrations of limonene metabolites were lower than those at the 4 h time point. Similar time courses have been described in rats, where the highest concentrations of limonene-derived material are present between 2 and 12 h post-ingestion, and are declining by 24 h post-ingestion. Thus, all available data suggest that the rat is a suitable model for human limonene metabolism and disposition.

TABLE 4

Retention times and on-line GC/IR analyses of human limonene metabolites[a]

| Compound | Retention time (min) | IR absorbance (cm$^{-1}$) |
| --- | --- | --- |
| H1 | 9.60 | ND |
| Dihydroperillic acid methyl ester | 9.60 | ND |
| H2 | 9.79 | ND |
| Limonene-1,2-diol | 9.79 | ND |
| H3 | 10.46 | 1770(s, C=O); 3574, 1101(m, OH); 2944(m) |
| R3 (Dihydroperillic acid) | 10.46 | 1770(s, C=O); 3574, 1101(m, OH); 2944(m) |
| H4 | 10.70 | ND |
| Perillic acid methyl ester | 10.70 | ND |
| H5 | 11.42 | 1752(s, C=O); 3583, 1163(m, OH); 2948(w) |
| R5 (Perillic acid) | 11.42 | 1752(s, C=O); 3583, 1164(m, OH); 2943(w) |

TABLE 4-continued

Retention times and on-line GC/IR analyses of
human limonene metabolites[a]

| Compound | Retention time (min) | IR absorbance (cm$^{-1}$) |
| --- | --- | --- |

[a]The human limonene metabolite designations H1–H5 correspond to those in the text. The rat limonene metabolite designations R3 and R5 correspond to rat metabolites of limonene with the same retention times and mass spectra as those of the human limonene metabolites.

6. Inhibition of Lathesterol to Cholesterol

Materials and Methods

Analysis of Mevalonate Metabolism. NIH3T3 cells were grown in Dulbecco's modified Eagle's medium supplemented with 10% calf serum. Exponentially growing cells were treated with 30 MM lovastatin for 18 hours and then incubated in fresh medium containing 30 μM lovastatin and 7 μCi/ml (R,S)-[2-$^{14}$C] mevalonolactone (50 mCi/mmol, DuPont-New England Nuclear) for 3 hours in the absence or presence of 1 mM perillyl alcohol. The cells were then trypsinized, washed and resuspended in phosphate-buffered saline. The protein concentrations were determined using a bicinchoninic acid protein assay (Shihabi, et al, *Ann. Clin. Lab. Sci.* 18:235–239, 1988). Samples containing equal amount of protein were spotted on TLC plates with or without acetone extraction (Maziere, et al, *J. Biochem. Biophys. Methods* 14:267–272, 1987.) The TLC plates were developed with hexane/diethyl ether/acetic acid (70:30:2, v/v) (Maziere, et al, Supra). Dry plates were analyzed for radioactivity using a phosphorimager (Molecular Dynamics).

Labeling Cells with [$^{14}$C(U)] Tyrosine. NIH3T3 cells were treated with 30 μM lovastatin for 18 hours and then incubated in fresh tyrosine deficient minimum essential medium (supplemented with 10% dialyzed fetal bovine serum) containing 400 μM mevalonic acid lactone (Sigma) and 14 μCi/ml [$^{14}$C(U)] tyrosine (500 mCi/mmol) for 3 hours in the absence or presence of 1 mM perillyl alcohol. Cells were harvested and lipids were analyzed as described above.

HPLC Analysis of Unsaponifiable Lipids. Cells were labeled with [2-$^{14}$C] mevalonolactone as described above and then were saponified as described by Popjak et al, *J. Lipid Res,* 26:831–841, 1985. Unsaponifiable lipids were extracted with petroleum ether, dried and dissolved in chloroform methanol (1:1, v/v). Reverse phase HPLC using a Bio-Rad ODS-5S (25 cm×4 mm) column fitted with a Sigma hypersil ODS guard column was run isocratically with methanol/acetonitrile/water (72.5:22.5:5, v/v) at a flow rate of 0.8 ml/min. The effluent was monitored at 210 nm, the fractions were collected, and radioactivities were determined with a Beckman LS 6000IC Scintillation Counter.

Results

The effects of perillyl alcohol on mevalonate metabolism are as follows: Three major changes of neutral lipid metabolism observed in perillyl alcohol treated cells included the inhibition of two spots (X and Y) and the increased accumulation of a third spot (Z). Spot X was identified as CoQ9 by its comigration with authentic CoQ9 standard (Sigma) in both one-dimensional and several two-dimensional TLC systems (data not shown). In addition, this tentative identification of spot X was verified by labeling the cells with $^{14}$C(U)-tyrosine, a precursor of CoQ9. Following the labeling, only one neutral lipid was resolved by TLC. It comigrated with authentic CoQ9 standard in several one-dimensional and two-dimensional TLC systems (data not shown) and was greatly reduced in perillyl alcohol treated cells. Similar results were obtained when cells were labeled with another precursor of CoQ9, [$^{14}$C(U)ring]-4-hydroxybenzoate (data not shown).

When cells were labeled with [$^{14}$C]squalene, the inhibition of spot Y and the accumulation of spot Z were also observed in perillyl alcohol treated cells. Neither spot comigrated with squalene (data not shown). As expected, CoQ9 was not labeled following [$^{14}$C]squalene labeling. Spot Y comigrated with an authentic cholesterol standard (Sigma) on TLC plate. When cells were labeled with [26-$^{14}$C] cholesterol, only one spot was seen in both control and perillyl alcohol treated cells at the position of spot Y. Thus, spot Y was identified as cholesterol while spot Z was likely to be a compound between squalene and cholesterol in the cholesterol synthesis pathway.

Because the TLC system used above could not separate all intermediates of cholesterol synthesis, an HPLC system was used to analyze the unsaponifiable lipids extracted from cells labeled with [2-$^{14}$C] mevalonolactone. By HPLC analysis using authentic standards, spot Y was confirmed to be cholesterol and spot Z was identified as lathosterol. The identities of spot Y and Z were further confirmed to be cholesterol and lathosterol by gas chromatography-mass spectrometry (data not shown). The qualitative results described above were quantitated. The perillyl alcohol-induced decreases in CoQ9 and cholesterol and the increase in lathosterol are given in Table 5.

TABLE 5

Inhibition of CoQ9 and
Cholesterol Synthesis by Perillyl Alcohol

| Compounds | Synthesis in 1 mM Perillyl Alcohol Medium (% of Control) |
| --- | --- |
| CoQ9 | 14.1 ± 4.6 |
| Cholesterol | 26.7 ± 4.7 |
| Lathosterol | 427.3 ± 129.6 |
| Cholesterol + Lathosterol | 106.8 ± 16.5 |

NIH3T3 cells were labeled with [2-$^{14}$C] mevalonolactone and neutral lipids were analyzed by TLC as described in the experimental procedures. Quantifications of CoQ9, cholesterol and lathosterol spots were done using a phosphorimager. The result is the average of four independent experiments ± SD.

In order to determine if the perillyl alcohol-induced inhibition of CoQ9 and cholesterol syntheses were reversible, cells were labeled with [2-$^{14}$C]-mevalonolactone in the presence of 1 mM perillyl alcohol for an initial period of 3 hours. Cells were then switched to control medium for a 3 hour chase period. Lathosterol was observed to be converted to cholesterol during this time interval. In contrast, cells that were continually grown in 1 mM perillyl alcohol median during this period maintained the block of cholesterol synthesis. Cells that were reincubated in 1 mM perillyl alcohol medium after growing for 3 hours in control medium did not convert labeled cholesterol back to labeled lathosterol. Finally, it should be noted that labeled CoQ9 could not be observed even if the cells were incubated in fresh cold control medium for up to 6 hours post-labeling.

7. Effect of Perillyl Alcohol On Serum Cholesterol And CoO levels

Twenty-one female, six-weeks-old, Wistar-Furth rats were divided into three different diet groups of seven rats each. One group was fed a control diet, one group was fed a 1% perillyl alcohol diet, and one group was fed a 2% perillyl alcohol diet. Rats from each diet group were matched into pair feeding groups.

Rats in the control group were pair fed against rats in the 2% POH diet group. Rats in the 1% POH diet group were allowed to eat as much as they wanted. After one month, rats in the 1% POH diet group were also pair fed against rats in 2% POH group. After two months of feeding, rats in all groups were allowed to eat as much as they wanted. The rats were allowed to eat as much as they wanted because the diurnal rhythm of HMGCoA reductase activity might be related to food intake.

The rats' body weights were measured twice a week. Perillyl alcohol diets were made once a week and replaced daily.

Rats' blood was taken through eye bleeding once a day. About 1 ml blood was taken from each rat each time and collected in heparin (SIGMA) coated tube. For CoQ analysis, 0.5 ml blood was added to the CoQ6 standard. For cholesterol analysis the blood were spun down at 3,000 rpm for 10 minutes and the plasma were taken. By three months, all rats were killed.

Total cholesterol, HDL cholesterol and triglyceride levels in the rats' plasma were measured using diagnostic kits from SIGMA according to manufacturer's instructions. LDL cholesterol levels were calculated by Friedewald's equation.

CoQ9 and CoQ10 in blood and tissues were extracted and their levels were measured as described by Morita, et al. (*Biochemical and Biophysical Research Communications*, 191:950–954, 1993) with some modifications. Table 6 shows our results.

TABLE 6

| Group | WK3 | WK6 | WK9 | Kill |
|---|---|---|---|---|
| Total Cholesterol (mg/dL) | | | | |
| Control* | 72.4 ± 10.1 | 67.8 ± 5.9 | 54.1 ± 7.2 | 64.7 ± 6.2 |
| 1% POH* | 45.9 ± 4.2 | 41.0 ± 3.0 | 43.2 ± 4.9 | 47.7 ± 4.3 |
| 2% POH* | 44.2 ± 3.7 | 41.2 ± 5.0 | 40.7 ± 3.3 | 52.8 ± 6.8 |
| HDL Cholesterol (mg/dL) | | | | |
| Control* | 42.2 ± 3.3 | 47.9 ± 3.7 | 36.3 ± 4.6 | 45.5 ± 2.2 |
| 1% POH* | 31.7 ± 2.3 | 33.1 ± 2.2 | 31.5 ± 2.6 | 37.6 ± 3.8 |
| 2% POH* | 31.4 ± 1.6 | 33.5 ± 3.6 | 30.7 ± 2.9 | 39.8 ± 4.0 |
| LDL Cholesterol (mg/dL) | | | | |
| Control* | 21.6 ± 6.9 | 11.1 ± 4.3 | 11.4 ± 3.1 | 9.2 ± 3.5 |
| 1% POH* | 10.1 ± 3.1 | 2.0 ± 1.4 | 6.0 ± 4.0 | 4.1 ± 2.4 |
| 2% POH* | 9.4 ± 3.0 | 3.4 ± 2.2 | 6.4 ± 1.2 | 6.2 ± 1.8 |
| Triglyceride (mg/dL) | | | | |
| Control* | 43.3 ± 11.0 | 44.2 ± 11.1 | 31.4 ± 7.4 | 49.9 ± 13.5 |
| 1% POH* | 20.8 ± 5.2 | 29.5 ± 5.7 | 28.7 ± 5.7 | 29.8 ± 8.9 |
| 2% POH* | 17.2 ± 5.3 | 21.1 ± 5.7 | 18.4 ± 2.9 | 33.8 ± 14.9 |

| Group | Control* | 1% POH* | 2% POH* |
|---|---|---|---|
| Body Weight (g) | 204 ± 6 | 207 ± 3 | 198 ± 6 |
| Liver Weight (g) | 5.3 ± 0.4 | 6.1 ± 0.3 | 6.2 ± 0.5 |
| Heart Weight (g) | 0.57 ± 0.04 | 0.57 ± 0.05 | 0.57 ± 0.05 |

*n = 7

We note that after 6 weeks of treatment, the total cholesterol level is reduced in the perillyl alcohol-treated animals. The LDL level is reduced much more than the HDL level. Triglyceride levels are also dramatically reduced after 6 weeks of treatment.

8. Dietary Perillic Acid Methyl Ester-induced Rat Mammary Tumor Regression in WF Rats Given 50 mg/kg DMBA.

Inbred female Wistar-Furth rats were given 50 mg/kg DMBA at 50–55 days of age. Upon development of a mammary tumor with the largest diameter ≧ 10 mm, the rat was assigned to 0.5% perillic acid methyl ester diet and fed ad libitum. The 0.5% perillic acid methyl ester diet (weight compound/weight ground Teklad rat/mouse 4% meal/chow) was prepared fresh every 7–10 days. Fresh diet was given to rats daily. All rats were weighed and palpated weekly. The study was terminated at 6 weeks after initial diet administration. The following tumor regression data was acquired:

TABLE 7

| rat # | size change | time |
|---|---|---|
| 24 | 12→25 mm | 6 wks |
| 25 | 12→6 mm | 5 wks |
| 26 | 10→3 mm | 4 wks |
| 27 | 10→5 mm | 4 wks |
| 28 | 12→15 mm | 6 wks |
| 29 | 15→15 mm | 6 wks |
| 29 | 10→3 mm | 3 wks |
| 30 | 20→30 mm | 2 wks |
| 31 | 15→18 mm | 6 wks |
| 31 | 12→8 mm | 6 wks |
| 32 | 10→8 mm | 6 wks |
| 32 | 10→5 mm | 5 wks |
| 33 | 10→8 mm | 6 wks |
| 34 | 10→5 mm | 4 wks |
| 35 | 10→12 mm | 6 wks |
| 36 | 10→4 mm | 3 wks |
| 37 | 10→4 mm | 3 wks |
| 38 | 10→6 mm | 5 wks |
| 38 | 10→6 mm | 6 wks |

In summary, 9 of 19 tumors had regressed to greater than or equal to one half the original diameter within 6 weeks. 10 of 19 tumors had not regressed. 4 of 19 tumors had a small regression response. 5 of 19 had some growth. 1 tumor did not respond.

Comparison of Efficacy of Dietary Perillyl Alcohol And Perillic Acid Methyl Ester As Inducers Of Rat Mammary Carcinoma Regression We compared the effects of PAME and POH in terms of their ability to regress rat mammary carcinomas. Table 8 records our comparison. In summary, a 0.5% PAME diet was effective, while a 0.5% POH diet was only 10% effective. Diets of 2% POH were roughly 64–70% effective. While 2% POH is tolerated by a mammal, on a practical level PAME is preferred because a lower dose is sufficient. Moreover, the rats fed PAME did not lose weight, while the POH-fed rats did experience weight loss.

TABLE 8

| | *These results reflect palpation data thru 6 weeks post-initial diet assignment | | | |
|---|---|---|---|---|
| | partial regression >½ original diameter | | no regression | |
| Second Comparison | | | | |
| 0.5% PAME diet | 9/19 | 47% | 10/19 | 5/19 some growth of tumor |

TABLE 8-continued

*These results reflect palpation data thru 6 weeks post-initial diet assignment

| | partial regression >½ original diameter | | no regression | | |
|---|---|---|---|---|---|
| 2.0% POH diet | 7/11 | 64% | 4/11 | 1/19 | no response |
| | | | | 4/19 | small regression response |
| | | | | 1/11 | some growth of tumor |
| | | | | 2/11 | no response |
| | | | | 1/11 | small regression response |
| First Comparison | | | | | |
| 0.5% POH diet | 2/20 | 10% | 18/20 | 15/20 | some growth of tumor |
| | | | | 1/20 | no response |
| | | | | 2/20 | small regression response |
| 1.0% POH diet | 5/20 | 25% | 15/20 | 11/20 | some growth of tumor |
| | | | | 2/20 | no response |
| | | | | 2/20 | small regression response |
| 1.5% POH diet | 6/21 | 29% | 15/21 | 4/21 | some growth of tumor |
| | | | | 7/21 | no response |
| 2.0% POH diet | 14/20 | 70% | 6/20 | 7/21 | small regression response |
| | | | | 3/20 | some growth of tumor |
| | | | | 1/20 | no response |
| | | | | 2/20 | small regression response |

We claim:

1. A method for causing the regression of a carcinoma, comprising the step of administering to a carcinoma-containing mammal an effective amount of perillic acid methyl ester, wherein after the administration the carcinoma is smaller in size than its size at the beginning of said administering step.

2. The method of claim 1, wherein the administration comprises the dose of between 0.028 and 0.064 grams per kg human weight.

3. The method of claim 2 wherein the dose is between 0.036 and 0.043 grams per day per kg human weight.

* * * * *